(12) United States Patent
Stayton et al.

(10) Patent No.: US 9,080,933 B2
(45) Date of Patent: Jul. 14, 2015

(54) STIMULI-RESPONSIVE POLYMER DIAGNOSTIC ASSAY COMPRISING MAGNETIC NANOPARTICLES AND CAPTURE CONJUGATES

(71) Applicant: University of Washington through its Center for Commercialization, Seattle, WA (US)

(72) Inventors: Patrick S. Stayton, Seattle, WA (US); Jriuan Lai, Seattle, WA (US); Barrett J. Nehilla, Seattle, WA (US); Selvi Srinivasan, Seattle, WA (US)

(73) Assignee: University of Washington through its Center for Commercialization, Seattle, WA (US)

( * ) Notice: Subject to any disclaimer, the term of this patent is extended or adjusted under 35 U.S.C. 154(b) by 36 days.

(21) Appl. No.: 13/891,005

(22) Filed: May 9, 2013

(65) Prior Publication Data

US 2013/0295585 A1    Nov. 7, 2013

Related U.S. Application Data

(63) Continuation of application No. PCT/US2011/035256, filed on May 4, 2011, which is a continuation-in-part of application No. 12/942,919, filed on Nov. 9, 2010, now abandoned.

(60) Provisional application No. 61/259,545, filed on Nov. 9, 2009.

(51) Int. Cl.
| | |
|---|---|
| *G01N 1/34* | (2006.01) |
| *C12Q 1/68* | (2006.01) |
| *B82Y 25/00* | (2011.01) |
| *G01N 1/00* | (2006.01) |
| *B01D 21/00* | (2006.01) |
| *C12N 15/10* | (2006.01) |
| *G01N 27/74* | (2006.01) |
| *G01N 33/543* | (2006.01) |
| *B03C 1/01* | (2006.01) |
| *B03C 1/28* | (2006.01) |
| *G01N 1/40* | (2006.01) |

(52) U.S. Cl.
CPC ............ *G01N 1/34* (2013.01); *B01D 21/0009* (2013.01); *B03C 1/01* (2013.01); *B03C 1/288* (2013.01); *B82Y 25/00* (2013.01); *C12N 15/1013* (2013.01); *C12Q 1/6834* (2013.01); *G01N 27/745* (2013.01); *G01N 33/54333* (2013.01); *B03C 2201/18* (2013.01); *B03C 2201/26* (2013.01); *G01N 2001/4038* (2013.01); *G01N 2001/4088* (2013.01); *Y10T 436/00* (2015.01); *Y10T 436/25* (2015.01)

(58) Field of Classification Search
CPC .......... G01N 1/34; G01N 1/00; Y10T 436/25; Y10T 436/00; C12Q 1/6834; C12Q 1/68; C12Q 2563/143; C12Q 2563/00; B82Y 25/00

USPC ................. 436/178, 174, 501; 435/7.1, 4
See application file for complete search history.

(56) References Cited

U.S. PATENT DOCUMENTS

| | | |
|---|---|---|
| 4,332,690 A | 6/1982 | Kimura |
| 4,657,543 A | 4/1987 | Langer |
| 4,780,409 A | 10/1988 | Monji |
| 5,135,876 A | 8/1992 | Andrade |
| 5,356,713 A | 10/1994 | Charmot |
| 5,362,308 A | 11/1994 | Chien |
| 5,378,608 A | 1/1995 | Marui |
| 5,451,411 A | 9/1995 | Gombotz |
| 5,466,348 A | 11/1995 | Holm-Kennedy |
| 5,501,584 A | 3/1996 | Yamamoto |
| 5,521,291 A | 5/1996 | Curiel |
| 5,547,932 A | 8/1996 | Curiel |
| 5,569,364 A | 10/1996 | Hooper |
| 5,599,908 A | 2/1997 | Raso |
| 5,603,931 A | 2/1997 | Raso |
| 5,609,590 A | 3/1997 | Herbig |
| 5,656,609 A | 8/1997 | Wu |
| 5,753,263 A | 5/1998 | Lishko |
| 5,770,627 A | 6/1998 | Inoue |
| 5,807,306 A | 9/1998 | Shapland |
| 5,827,743 A | 10/1998 | Tanzawa |
| 5,876,989 A | 3/1999 | Berg |

(Continued)

FOREIGN PATENT DOCUMENTS

| | | |
|---|---|---|
| DE | 697 06 501 T2 | 5/2002 |
| DE | 102 24 352 A1 | 12/2003 |

(Continued)

OTHER PUBLICATIONS

Akiyoshi, K., et al., "Controlled Association of Amphiphilic Polymers in Water: Thermosensitive Nanoparticles Formed by Self-Assembly of Hydrophobically Modified Pullulans and Poly(N-isopropylacrylamides)," Macromolecules 33(9):3244-3249, May 2000.

Buchholz, B.A., et al., "Microchannel DNA Sequencing Matrices With Switchable Viscosities," Electrophoresis 23(10):1398-1409, May 2002.

Frey, N.A., et al., "Magnetic Nanoparticles: Synthesis, Functionalization, and Applications in Bioimaging and Magnetic Energy Storage," Chemical Society Reviews 38(9):2532-2542, Sep. 2009.

Golden, A., et al., "Simple Fluidic System for Purifying and Concentrating Diagnostic Biomarkers Using Stimuli-Responsive Antibody Conjugates and Membranes," Bioconjugate Chemistry 21(10):1820-1826, Oct. 2010.

(Continued)

*Primary Examiner* — Christine T Mui
(74) *Attorney, Agent, or Firm* — Christensen O'Connor Johnson Kindness PLLC

(57) ABSTRACT

The present disclosure utilizes the aggregation of stimuli-responsive polymers to isolate a diagnostic target (e.g., an antigen) from a solution using magnetophoresis. Isolating the diagnostic target provides a route to identify the presence of the diagnostic target in the solution.

26 Claims, 9 Drawing Sheets

(56) References Cited

U.S. PATENT DOCUMENTS

| | | |
|---|---|---|
| 5,939,453 A | 8/1999 | Heller |
| 5,997,961 A | 12/1999 | Feng |
| 5,998,588 A | 12/1999 | Hoffman |
| 6,133,047 A | 10/2000 | Elaissari |
| 6,165,509 A | 12/2000 | Hoffman |
| 6,210,717 B1 | 4/2001 | Choi |
| 6,355,163 B2 | 3/2002 | Hindsgaul |
| 6,426,086 B1 | 7/2002 | Papahadjopoulos |
| 6,447,764 B1 | 9/2002 | Bayer |
| 6,486,213 B1 | 11/2002 | Chen |
| 6,521,341 B1 | 2/2003 | Elaissari |
| 6,641,735 B1 | 11/2003 | Yoshizako |
| 6,740,409 B1 | 5/2004 | Granick |
| 6,835,393 B2 | 12/2004 | Hoffman |
| 7,060,804 B2 | 6/2006 | Elaissari |
| 7,195,925 B2 | 3/2007 | Ohnishi |
| 7,393,698 B2 | 7/2008 | Furukawa |
| 7,625,764 B2 | 12/2009 | Stayton |
| 7,695,905 B2 | 4/2010 | Furukawa |
| 7,718,193 B2 | 5/2010 | Stayton |
| 7,732,550 B2 | 6/2010 | Ohnishi |
| 7,976,728 B2 | 7/2011 | Eguchi |
| 7,981,688 B2 | 7/2011 | Stayton |
| 8,105,493 B2 | 1/2012 | Takahashi |
| 2001/0027072 A1 | 10/2001 | Mumick |
| 2003/0165962 A1 | 9/2003 | Furukawa |
| 2003/0175691 A1 | 9/2003 | Elaissari |
| 2003/0175826 A1 | 9/2003 | Furukawa |
| 2003/0218130 A1 | 11/2003 | Boschetti |
| 2004/0077024 A1 | 4/2004 | Holmberg |
| 2004/0239738 A1 | 12/2004 | Watanabe |
| 2005/0124728 A1 | 6/2005 | Komatsu |
| 2005/0130167 A1 | 6/2005 | Bao |
| 2005/0137334 A1 | 6/2005 | Mondain-Monval |
| 2005/0158782 A1 | 7/2005 | Furukawa |
| 2005/0175702 A1 | 8/2005 | Müller-Schulte |
| 2006/0127925 A1 | 6/2006 | Stayton |
| 2007/0140974 A1* | 6/2007 | Torres et al. ............... 424/9.323 |
| 2007/0218567 A1 | 9/2007 | Tanaka |
| 2008/0199884 A1 | 8/2008 | Ohnishi |
| 2008/0220531 A1 | 9/2008 | Stayton |
| 2008/0293118 A1 | 11/2008 | Furukawa |
| 2009/0001025 A1 | 1/2009 | Takahashi |
| 2009/0001321 A1 | 1/2009 | Eguchi |
| 2010/0062433 A1 | 3/2010 | Nagaoka |
| 2010/0168044 A1 | 7/2010 | Misra |
| 2010/0215749 A1 | 8/2010 | Stayton |
| 2010/0330688 A1 | 12/2010 | Sawai |
| 2011/0003392 A1 | 1/2011 | Stayton |
| 2011/0014713 A1 | 1/2011 | Sawai |
| 2011/0097416 A1 | 4/2011 | Nguyen |
| 2011/0117668 A1 | 5/2011 | Stayton |
| 2011/0120919 A1 | 5/2011 | Domke |
| 2011/0155947 A1 | 6/2011 | Eguchi |
| 2011/0233453 A1 | 9/2011 | Eguchi |
| 2011/0266492 A1 | 11/2011 | Stayton |

FOREIGN PATENT DOCUMENTS

| | | |
|---|---|---|
| DE | 698 39 323 T2 | 4/2009 |
| EP | 0 693 508 A1 | 1/1996 |
| EP | 1 281 436 A1 | 2/2003 |
| EP | 1 312 671 A1 | 5/2003 |
| EP | 1 316 599 A1 | 6/2003 |
| EP | 1 396 508 A1 | 3/2004 |
| EP | 1 803 467 A1 | 7/2007 |
| EP | 2 009 044 A1 | 12/2008 |
| EP | 2 009 442 A2 | 12/2008 |
| EP | 2 037 272 A1 | 3/2009 |
| EP | 1 509 246 B1 | 5/2009 |
| EP | 2 237 036 A1 | 10/2010 |
| EP | 2 246 701 A1 | 11/2010 |
| EP | 2 313 200 A1 | 4/2011 |
| EP | 2 320 437 A1 | 5/2011 |
| GB | 2439846 B | 10/2009 |
| GB | 2435647 B | 3/2010 |
| GB | 2431472 B | 4/2011 |
| JP | 2002-223793 A | 8/2002 |
| JP | 2004-201648 A | 7/2004 |
| JP | 2005-60244 A | 3/2005 |
| JP | 2005-82538 A | 3/2005 |
| JP | 2005-537342 A | 12/2005 |
| JP | 2006-194635 A | 7/2006 |
| JP | 2006-208368 A | 8/2006 |
| JP | 2006-242597 A | 9/2006 |
| JP | 2006-327962 A | 12/2006 |
| JP | 2007-56094 A | 3/2007 |
| JP | 2007-248349 A | 9/2007 |
| JP | 2007-256024 A | 10/2007 |
| JP | 2007-262388 A | 10/2007 |
| JP | 2008-232716 A | 10/2008 |
| JP | 2009-13207 A | 1/2009 |
| JP | 2009-28711 A | 2/2009 |
| JP | 2009-162532 A | 7/2009 |
| JP | 2009-162534 A | 7/2009 |
| JP | 2009-171853 A | 8/2009 |
| JP | 2009-281728 A | 12/2009 |
| JP | 2010-32360 A | 2/2010 |
| JP | 2010-62444 A | 3/2010 |
| JP | 2010-66200 A | 3/2010 |
| JP | 2010-151528 A | 7/2010 |
| JP | 2010-235441 A | 10/2010 |
| WO | 00/43355 A1 | 7/2000 |
| WO | 01/51092 A2 | 7/2001 |
| WO | 02/16528 A1 | 2/2002 |
| WO | 02/16571 A1 | 2/2002 |
| WO | 03/055590 A2 | 7/2003 |
| WO | 2005/021612 A1 | 3/2005 |
| WO | 2006/022340 A1 | 3/2006 |
| WO | 2008/111687 A1 | 9/2008 |
| WO | 2009/084595 A1 | 7/2009 |
| WO | 2009/126441 A1 | 10/2009 |
| WO | 2009/140421 A2 | 11/2009 |
| WO | 2009/140429 A2 | 11/2009 |
| WO | 2009/140432 A2 | 11/2009 |
| WO | 2010/007157 A1 | 1/2010 |
| WO | 2010/021770 A1 | 2/2010 |
| WO | 2010/053597 A2 | 5/2010 |

OTHER PUBLICATIONS

Guo, J., et al., "Poly(N-isopropylacrylamide)-Coated Luminescent/Magnetic Silica Microspheres: Preparation, Characterization, and Biomedical Applications," Chemistry of Materials 18(23):5554-5562, Nov. 2006.

Hoffman, A.S., et al., "Really Smart Bioconjugates of Smart Polymers and Receptor Proteins," Journal of Biomedical Materials Research 52(4):577-586, Dec. 2000.

Hoffman, J.M., et al., "A Helical Flow, Circular Microreactor for Separating and Enriching 'Smart' Polymer—Antibody Capture Reagents," Lab on a Chip 22(10):3130-3138, Nov. 2010.

International Search Report and Written Opinion mailed Sep. 15, 2011, issued in corresponding International Application No. PCT/US2011/035256, filed May 4, 2011, 12 pages.

International Search Report and Written Opinion mailed Feb. 22, 2012, issued in corresponding International Application No. PCT/US2011/040385, filed Jun. 14, 2011, 10 pages.

Irie, M., "Stimuli-Responsive Poly(N-isopropylacrylamide). Photo- and Chemical-Induced Phase Transitions," in K. Dušek (ed.), vol. 110, "Responsive Gels: Volume Transitions II," "Advances in Polymer Science," Springer-Verlag, Berlin, 1993, pp. 49-65.

Kanazawa, H., and Y. Matsushima, "Temperature-Responsive Chromatography," Trends in Analytical Chemistry 17(7):435-440, Aug. 1998.

Kondo, A., and H. Fukuda, "Preparation of Thermo-Sensitive Magnetic Hydrogel Microspheres and Application to Enzyme Immobilization," Journal of Fermentation and Bioengineering 84(4):337-341, Jan. 1997.

Kondo, A., et al., "Development and Application of Thermo-Sensitive Magnetic Immunomicrospheres for Antibody Purification," Applied Microbiology and Biotechnology 41(1):99-105, Mar. 1994.

(56) References Cited

OTHER PUBLICATIONS

Kulkarni, S., et al., "Reversible Meso-Scale Smart Polymer—Protein Particles of Controlled Sizes," Bioconjugate Chemistry 15(4):747-753, Jul.-Aug. 2004.

Lai, J.J., et al., "Dual Magnetic-/Temperature-Responsive Nanoparticles for Microfluidic Separations and Assays," Langmuir 23(13)1385-7391, Jun. 2007.

Li, M., et al., "Organization of Inorganic Nanoparticles Using Biotin-Streptavidin Connectors," Chemistry of Materials 11(1):23-26, Jan. 1999.

Malmstadt, N., et al., "A Smart Microfluidic Affinity Chromatography Matrix Composed of Poly(N-isopropylacrylamide)-Coated Beads," Analytical Chemistry 75(13)2943-949, Jul. 2003.

Malmstadt, N., et al., "'Smart' Mobile Affinity Matrix for Microfluidic Immunoassays," Lab on a Chip 4(4):412-415, Aug. 2004.

Matsubara, C., et al., "Determination of Trace Amounts of Phosphate in Water After Preconcentration Using a Thermally Reversible Polymer," Analyst 118(5):553-556, May 1993.

Miura, M., et al., "Application of LCST Polymer-Cell Receptor Conjugates for Cell Culture on Hydrophobic Surfaces," 17th Annual Meeting of the Society for Biomaterials, Scottsdale, Ariz., May 1-5, 1991, p. 130.

Monji, N., and A.S. Hoffman, "A Novel Immunoassay System and Bioseparation Process Based on Thermal Phase Separating Polymers," Applied Biochemistry and Biotechnology 14(2):107-120, Mar. 1987.

Monji, N., et al., "Application of a Thermally-Reversible Polymer—Antibody Conjugate in a Novel Membrane-Based Immunoassay," Biochemical and Biophysical Research Communications 172(2):652-660, Oct. 1990.

Nash, M.A., et al., "Mixed Stimuli-Responsive Magnetic and Gold Nanoparticle System for Rapid Purification, Enrichment, and Detection of Biomarkers," Bioconjugate Chemistry 21(12):2197-2204, Dec. 2010.

Nash, M.A., et al., "'Smart' Diblock Copolymers as Templates for Magnetic-Core Gold-Shell Nanoparticle Synthesis," Nano Letters 10(1):85-91, Jan. 2010.

Tang, Z., et al., "Single Nucleotide Polymorphisms (SNPs) Assay Using Reversible Association and Dispersion of DNA-Linked Colloidal Nanoparticles," Nucleic Acids Research: Supplement No. 1, Nov. 2001, pp. 165-166.

Yoshizako, K., and Y. Akiyama, "Regulation of Protein Binding Toward a Ligand on Chromatographic Matrixes by Masking and Forced-Releasing Effects Using Thermoresponsive Polymer," Analytical Chemistry 74(16):4160-4166, Aug. 2002.

Office Action from the European Patent Office mailed Mar. 13, 2015, issued in related Application No. 11 729 792.9, filed May 4, 2011, 7 pages.

\* cited by examiner

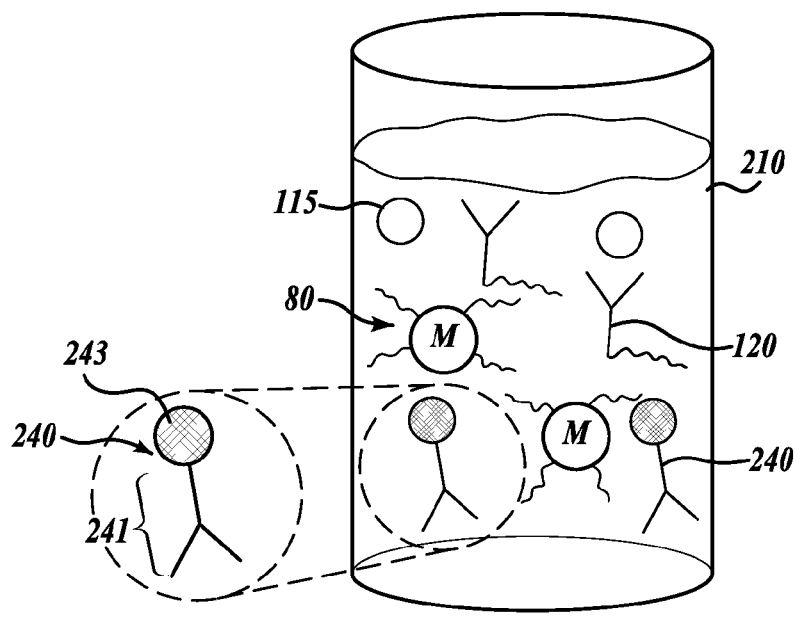
*Fig.3A.*
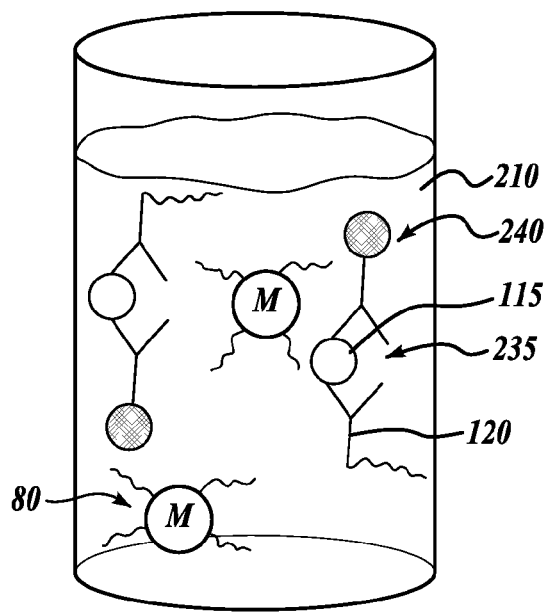 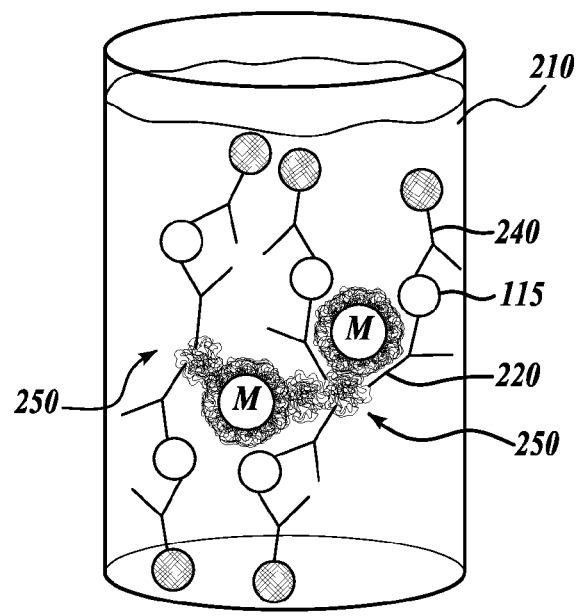
*Fig.3B.* *Fig.3C.*

STIMULI-RESPONSIVE POLYMER DIAGNOSTIC ASSAY COMPRISING MAGNETIC NANOPARTICLES AND CAPTURE CONJUGATES

CROSS-REFERENCES TO RELATED APPLICATIONS

This application is continuation of International Application No. PCT/US2011/035256, filed May 4, 2011, which is a continuation-in-part of U.S. application Ser. No. 12/942,919, filed Nov. 9, 2010, which claims the benefit of U.S. Provisional Application No. 61/259,545, filed Nov. 9, 2009, the disclosure of each is incorporated herein by reference in its entirety.

STATEMENT OF GOVERNMENT LICENSE RIGHTS

This invention was made with Government support under Contract Nos. EB000252 and EB002991, both awarded by the National Institutes of Health. The Government has certain rights in the invention.

BACKGROUND

The centralized hospital laboratory and the large reference laboratory remain the sites at which most clinical diagnostic testing, especially immunoassay testing, is done. There has been a convergence by the major manufacturers of immunoassay tests toward certain immunoassay formats. Among these, the sandwich immunoassay, employing both a trapping antibody and a detection antibody is the format of choice for analytes and biomarkers containing two separate epitopes to which antibodies can bind. There has been a further convergence by many leading immunoassay manufacturers on the use of antibody coupled magnetic beads as a separation means to enable the removal of the trapping antibody:antigen:detection antibody sandwich from unbound detection antibody. Magnetic beads have gained increasing use as a convenient separation technique for many forms of cell, nucleic acid and protein isolations and analyses. In particular, the manufacturers of clinical immunoassays utilize magnetic beads both as a solid support for antibodies targeted to analytes of clinical importance, and as the separation means to isolate and detect those bound analytes. Sandwich immunoassays, the most common immunoassay format, utilize two different antibodies—a trapping antibody (Ab) and a detection Ab—to form sandwich complexes in the presence of antigens. Magnetic microbeads provide an effective way to immobilize sandwich complexes while washing away unbound detection Ab. But use of magnetic beads imposes a paradox. The magnetic beads must have sufficient size—normally on the order of several microns in diameter—in order to be separated in an easily achievable magnetic field. But magnetic beads of this size diffuse only very slowly, and present very limited surface area for antibody binding compared to their volume. Thus the size of the current magnetic beads limits the speed and sensitivity that can be achieved in clinical immunoassays.

Through advances in template-directed polymer synthesis and nanotechnology, a new class of "smart" magnetic nanoparticles can be made. These magnetic nanoparticles can change from a monodispersed small diameter particle of roughly 20 nanometers diameter to a macro-aggregate of microns diameter in response to an environmental stimulus like a temperature or pH change. By using these advanced nanomaterials, assays can be developed in which the very high surface to volume ratio and the small size/high diffusion of the smart magnetic nanoparticles provides for higher sensitivity (greater antigen binding) and faster binding reactions compared to current magnetic bead reagents. A discrete pH or temperature stimulus can cause these smart nanoparticle reagents to co-aggregate with other entities containing stimuli-responsive polymers into a macro-aggregate of micron dimensions, which can be separated by a magnetic field as easily and quickly as currently used magnetic beads.

These new to the world materials present the promise of faster, more sensitive clinical immunoassays for important biomarkers of cardiac disease, cancer, endocrine and infectious diseases. These smart magnetic nanoparticles can show the same advantages in life science research applications currently using magnetic beads for the separation or analysis of cells, proteins, or nucleic acid sequences. The present invention seeks to fulfill this need and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a stimuli-responsive reagent is provided. In one embodiment, the stimuli-responsive reagent includes a stimuli-responsive magnetic nanoparticle that includes a first stimuli-responsive polymer attached to a magnetic core; and a stimuli-responsive capture conjugate that includes a second stimuli-responsive polymer attached to a first capture moiety, wherein the first capture moiety is capable of binding to a diagnostic target.

In another aspect, a method for concentrating a diagnostic target in a liquid is provided. In one embodiment, the method includes the steps of: applying a magnetic field to an aggregate in the liquid to provide a collected aggregate by magnetophoresis, wherein the aggregate includes: a stimuli-responsive magnetic nanoparticle comprising a first stimuli-responsive polymer attached to a magnetic core; and a stimuli-responsive capture conjugate that includes a second stimuli-responsive polymer attached to a capture moiety, wherein the capture moiety is capable of binding to a diagnostic target; wherein the aggregate is formed through associative interaction between the first stimuli-responsive polymer and the second stimuli-responsive polymer.

In another aspect, a method for capturing a diagnostic target in a liquid is provided. In one embodiment, the method includes the steps of:

(a) contacting a liquid to be tested for the presence of a diagnostic target with a stimuli-responsive reagent for a predetermined period of time sufficient to effect binding of the diagnostic target, if present, to the stimuli-responsive capture conjugate, comprising:
  (i) a stimuli-responsive magnetic nanoparticle comprising a first stimuli-responsive polymer attached to a magnetic core; and
  (ii) a stimuli-responsive capture conjugate comprising a second stimuli-responsive polymer attached to a capture moiety, wherein the capture moiety is capable of binding to a diagnostic target;

(b) applying an effective stimulus to provide an aggregate in the liquid formed through associative interaction between the first stimuli-responsive polymer and the second stimuli-responsive polymer, wherein the aggregate comprises (i) a stimuli-responsive magnetic nanoparticle comprising a first stimuli-responsive polymer attached to a magnetic core; and (ii) a stimuli-responsive capture conjugate comprising a second stimuli-responsive polymer attached to a capture moiety, wherein the capture moiety is bound to the diagnostic target when the diagnostic target is present in the liquid, (c) subjecting the aggregate to a magnetic field to magnetophorese the aggregate to a site within the liquid to provide a magnetophoresed aggregate in the liquid; and (d) analyzing the magnetophoresed aggregate to determine if the diagnostic target is present.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3A-3C are diagrammatic illustrations of an exemplary method for immobilizing a diagnostic target from a solution similar to that illustrated in FIGS. 2A-2F, although further comprising a reporting conjugate, in accordance with the embodiments provided herein;

DETAILED DESCRIPTION

The present invention utilizes the aggregation of stimuli-responsive polymers to isolate a diagnostic target (e.g., an antigen) from a solution using magnetophoresis. Isolating the diagnostic target provides a route to identify the presence of the diagnostic target in the solution. The systems and methods provided herein are not limited to a particular class of diagnostic target. Therefore, a universal method is provided for isolating a diagnostic target from a solution.

In the embodiments provided herein, stimuli-responsive polymers are coupled to both magnetic nanoparticles and capture moieties to form "smart" components of a reagent (a "smart reagent"). The smart magnetic nanoparticles and smart capture moieties are then combined in solution with a diagnostic target. In the combined solution, the smart capture moieties bind (or otherwise capture) the diagnostic target. Application of an effective stimulus (or stimuli) causes the stimuli-responsive polymers of both the smart magnetic nanoparticles and smart capture moieties, which are bound to the diagnostic target, to become associative such that the stimuli-responsive polymers aggregate in solution to form aggregates of the smart magnetic nanoparticles and smart capture moieties. The aggregates can then be further manipulated (e.g., isolated) and analyzed to identify the presence (or absence) of the diagnostic target.

Figure 1A:
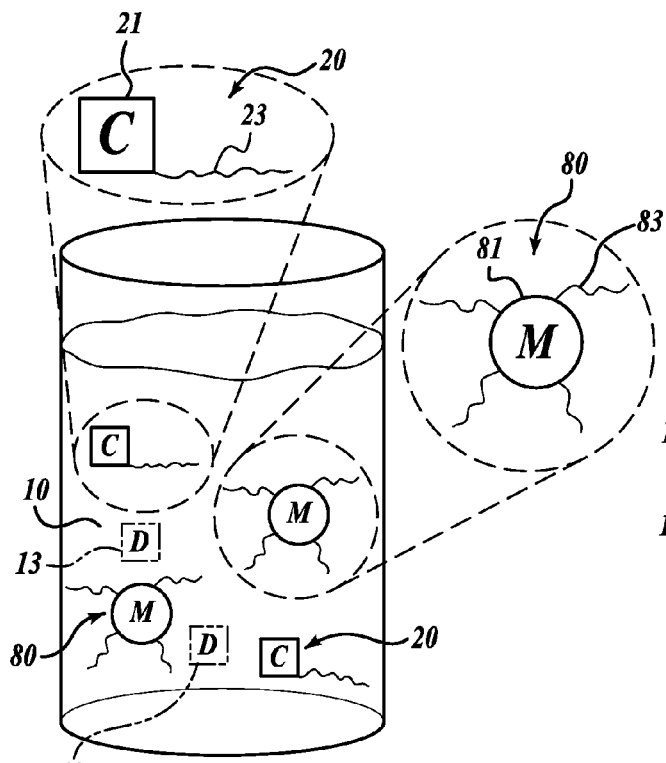
FIG. 1A-1H are diagrammatic illustrations of a method for isolating a diagnostic target from a solution using stimuli-responsive magnetic nanoparticles and capture conjugates in accordance with the embodiments provided herein.

FIGS. 1A-1H schematically illustrate an exemplary method for capturing a diagnostic target 15 from a solution 10 using stimuli-responsive magnetic nanoparticles 80 and stimuli-responsive capture conjugates 20, in accordance with the embodiments provided herein. Referring to FIG. 1A, a solution 10 includes a two-part reagent system comprising a plurality of stimuli-responsive magnetic nanoparticles 80 and a plurality of stimuli-responsive capture conjugates. The stimuli-responsive magnetic nanoparticles 80 (referred to herein as "smart mNPs") comprise a magnetic nanoparticle core 81 and a plurality of stimuli-responsive polymers 83 attached to the core 81. The stimuli-responsive capture conjugates 20 (referred to herein as "smart capture conjugates") comprise a capture moiety 21 and a stimuli-responsive polymer 23 attached to the capture moiety 21. The combination of the smart mNPs 80 and smart capture moieties 20 are referred to herein as a "smart reagent."

A plurality of detector complexes 13 can optionally be added to the solution 10 at any point during the process illustrated in FIGS. 1A-1H. In this regard, the detector complexes 13 are illustrated in phantom in FIGS. 1A-1H. The detector complexes 13 can be any complex having at least the ability to bind to the diagnostic target 15 and to provide (or otherwise facilitate) reporting of the detector complex 13. For example, in certain embodiments, the detector complex 13 comprises a fluorescent moiety and a detector binding moiety (e.g., an antibody). Detector complexes 13 are well known to those of skill in the art.

Figure 1B:
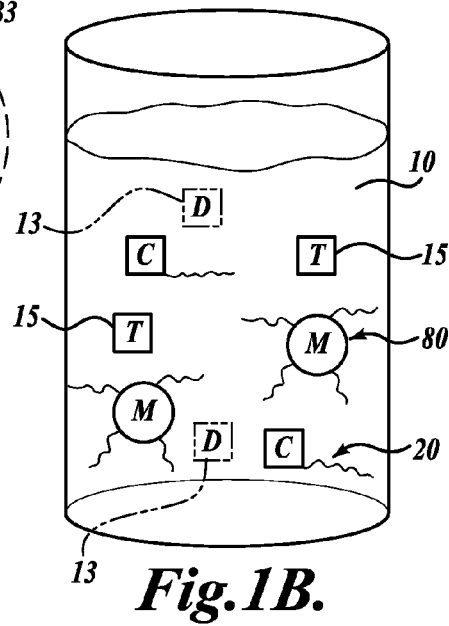
Figure 1C:
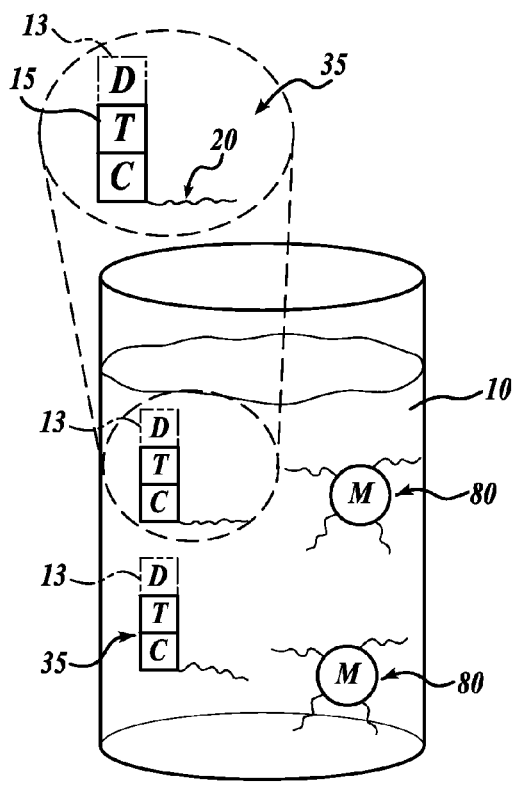
Figure 1D:
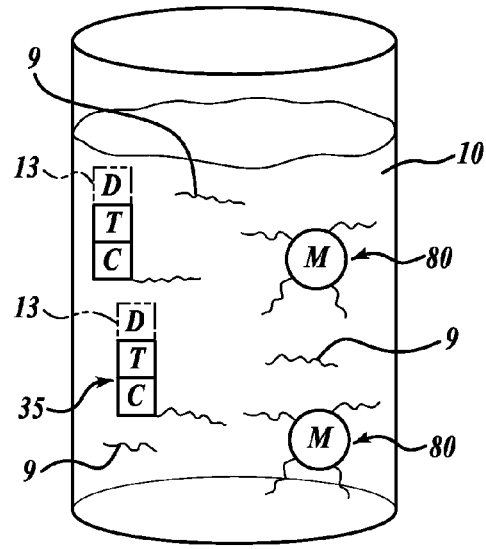

Referring to FIG. 1B, the smart reagent is combined in a solution 10 with a plurality of diagnostic targets 15 that will bind to a capture moiety 21. Accordingly, diagnostic target 15 in the solution 10 will bind to the capture moiety 21 of the capture conjugate 20 to form a capture complex 35, as illustrated in FIG. 1C.

To the solution 10 illustrated in FIG. 1C, certain embodiments provided herein include a step of adding stimuli-responsive polymer 9 to the solution so as to aid in stimuli-induced aggregation in later steps of the method. Optional detector complex 13 in the solution binds to the diagnostic target 15.

Figure 1E:
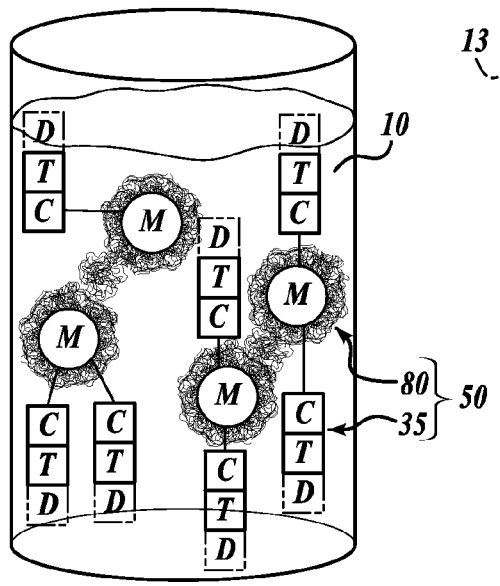

Referring to FIG. 1E, an effective stimulus (e.g., temperature change, pH change, or exposure to light) is applied to the solution 10 so as to cause the stimuli-responsive polymer moieties in the solution (e.g., 9, 23, and 83) to become (self)

associative, such that magnetic aggregates 50 are formed that comprise at least two smart mNP 80 and one smart capture complex 35.

The magnetic aggregates 50 can be isolated. Exemplary isolation methods are illustrated in FIGS. 1F-1H.

Figure 1F:
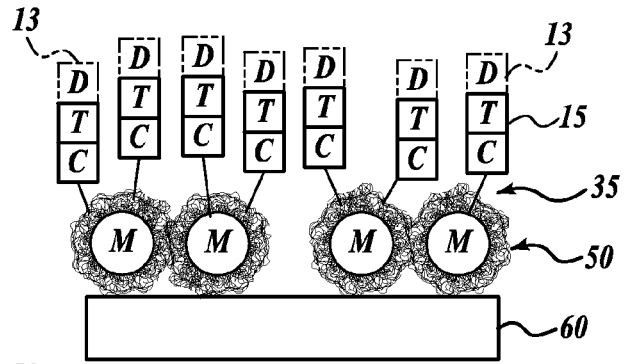
Figure 1G:
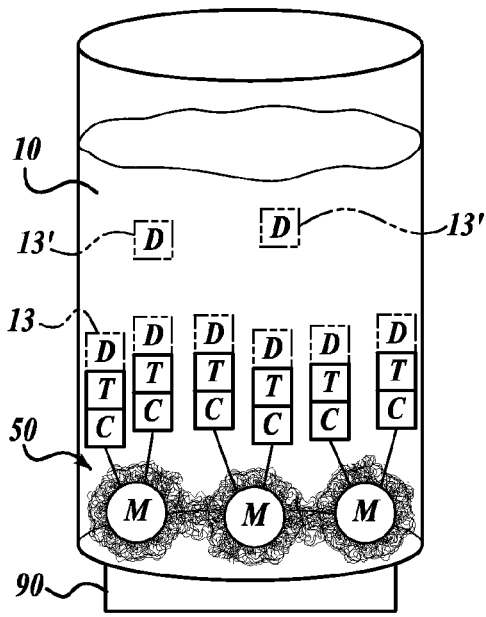
Figure 1H:
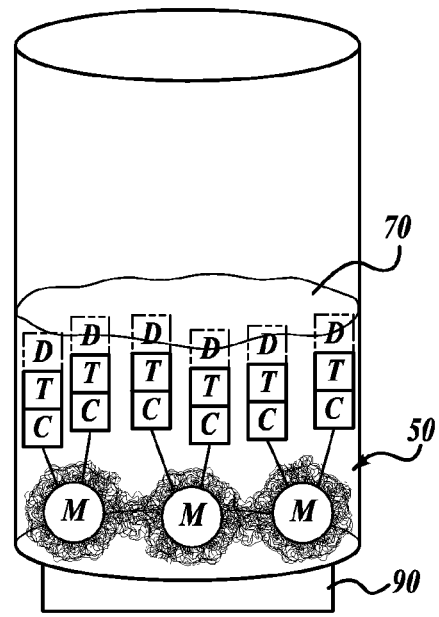

Referring to FIG. 1F, the magnetic aggregates 50 are isolated on a capture substrate 60. Representative capture substrates include filter paper having filter pores smaller than the magnetic aggregates 50, or having hydrophobic/hydrophilic properties such that the magnetic aggregates 50 are preferentially excluded from entering the filter 60.

In one embodiment, the aggregates 50 are pushed through the capture substrate 60 (e.g., filter) having a surface chemistry that adheres the aggregates 50 to membrane 60 upon contact. As illustrated in FIG. 1F, the membrane 60 collects the aggregates 50 from solution after the solution is passed through the capture substrate 60. The aggregates 50 are immobilized on the surface of the capture substrate 60.

Regarding immobilization of the aggregates 50 on the capture substrate 60, any mechanism for immobilization can be implemented in the present invention. Particularly useful are chemical adhesion means. Representative chemical adhesion means include hydrogen bonding between at least one moiety on the aggregate 50 and the capture substrate 60; and hydrophobic-hydrophobic (or hydrophilic-hydrophilic) associative binding. Associative binding can be between the aggregate 150 and an untreated membrane (e.g., hydroxylated nylon) or a membrane having temperature-responsive moieties attached thereto.

After immobilization, the aggregates 50 can be further processed to identify the diagnostic targets 15 using methods known to those of skill in the art. For example, the aggregates 50 can be washed with a solution, or series of solutions, containing the reagents to perform visual indication of the presence of the diagnostic target 15, such as an enzyme-based visual indicator or using a gold particle-based visual indicator known to those of skill in the art. Alternatively, the immobilized aggregates 50 can be re-solvated in a relatively small amount of solvent and tested by lateral flow or other techniques known to those of skill in the art.

If the detector complex 13 has been bound to the diagnostic target prior to the step illustrated in FIG. 1F, the detector complex 13 can be used to report the presence of the diagnostic target 15.

In certain embodiments, as illustrated in FIGS. 1G and 1H, a magnet 90 is used to concentrate the magnetic aggregates 50 in the solution 10 proximal to the magnet 90. Such magnetic concentration is only possible, in certain embodiments, when a plurality of magnetic nanoparticles 80 are aggregated together in the magnetic aggregates 50 such that the combined magnetic force acting in concert on the plurality of magnetic particles 80 is sufficient to ("magnetophorese") the magnetic aggregates 50 towards the magnet 90. If the magnetic aggregates 50 do not contain a sufficient number of magnetic nanoparticles 80, the magnetic force from the magnet 90 is not sufficient to move the magnetic aggregates 50 in the solution towards the magnet 90. For example, a single magnetic nanoparticle 80 will not have sufficient magnetic susceptibility to be attracted to a magnet 90 of typical magnetic strength.

In the embodiments provided herein, magnets are used for magnetophoresis to manipulate (e.g., move or concentrate) magnetic aggregates 50 in solution. The nature of the magnets described herein is not important, so long as the magnet produces a sufficient magnetic field to produce a force sufficient to move and concentrate the magnetic aggregates 50 as necessary. In certain embodiments, the magnets are permanent magnets, such as ceramic or neodymium-containing magnets. In certain embodiments, the magnets are electromagnets. In certain embodiments, the magnetic field has a strength of from 1 to 20 kilogauss.

Referring to FIG. 1G, a magnet 90 is provided adjacent the solution 10. The magnetic aggregates 50 magnetophorese toward the magnet 90 to concentrate the aggregates 50 near the magnet 90.

Referring to FIG. 1H, a solution 70 is similar to that of solution 10 illustrated in FIG. 1G, although the volume of the solution has been reduced so as to concentrate the magnetic aggregates 50 in the solution 70. Such a concentration step is typically accomplished by removing the supernatant above the magnetic aggregates 50 or other methods known to those of skill in the art.

After the magnetic aggregates 50 are concentrated in solution 70, such as in FIG. 1H, or concentrated on a surface 60, as in FIG. 1F, the magnetic aggregates 50 can then be analyzed using techniques known to those of skill in the art to detect the presence (or absence) of the diagnostic target 15 on the magnetic aggregates 50. Representative diagnostic techniques include immunoassays, electrochemical assays, enzyme or chemistry-based assays, culture techniques followed by chemical-based assays for identification and susceptibility testing, assays based on analytical techniques such as liquid chromatography, mass spectroscopy, electrophoresis and other techniques apparent to those of skill in the art.

Such magnetic techniques for isolating and immobilizing diagnostic targets 15 from a solution are the subject of U.S. patent application Ser. No. 12/815,217 filed Jun. 14, 2010 ("System and Method for Magnetically Concentrating and Detecting Biomarkers"), which is incorporated herein by reference in its entirety.

Both capture complexes with and without detector complexes 13 are useful in the provided embodiments. If a detector complex 13 has been added to the solution 10, any unbound (i.e., excess) detector complex 13' will be present in the supernatant, as illustrated in FIG. 1G. Excess detector complex 13' is removed from the solution by a technique known to those of skill in the art (e.g., by decanting and/or washing). A concentrated solution 70 results when the excess detector complexes 13' are removed. Accordingly, any reporting signal acquired from the solution 70 is the result of only detector complex 13 bound to a diagnostic target 15.

In certain embodiments, the solution 10 comprises a biological fluid that can be any fluid from an organism. Representative biological fluids are mammalian biological fluids, such as, for example, blood, mucus, urine, tissue, sputum, saliva, feces, a nasal swab, and nasopharyngeal washes.

The diagnostic target 15 is an analyte in the solution 10. Representative diagnostic targets include antibodies, antigens, cells, viruses, proteins, nucleic acids, and fragments thereof, as will be described in more detail below.

The systems and methods of the invention also include a magnetic particle bearing a stimuli-responsive polymer. As used herein, the term magnetic nanoparticle (MNP) describes a particle less than 100 nm in diameter that will magnetophorese when in a solution and exposed to a magnetic field of sufficient strength. In certain embodiments, the stimuli-responsive magnetic particles consist of a first stimuli-responsive polymer attached to a magnetic core.

Suitable magnetic particles are particles that are responsive to a magnetic field and magnetophorese through a medium in response to the application of a magnetic field. Representative magnetic particles include particles that include a suitable metal or metal oxide. Suitable metals and metal oxides include iron, nickel, cobalt, iron platinum, zinc selenide, ferrous oxide, ferric oxide, cobalt oxide, aluminum oxide, germanium oxide, tin dioxide, titanium dioxide, gadolinium oxide, indium tin oxide, cobalt iron oxide, magnesium iron oxide, manganese iron oxide, and mixtures thereof.

In one embodiment, the magnetic particles 80 are magnetic nanoparticles. In one embodiment, the magnetic nanoparticles have a largest dimension of from about 5 nanometers to about 100 nanometers.

Magnetic particles with attached smart polymers are known to those of skill in the art. For example, smart polymers can be conjugated to the surface of magnetic core. Alternatively, the magnetic core can be formed inside a micelle formed using stimuli-responsive polymers terminated with micelle-forming moieties, thereby embedding the micelle-forming moieties within the magnetic core. Such a technique for forming a smart mNP is described in U.S. Published Patent Application No. 2008/0220531, the disclosure of which is expressly incorporated herein by reference in its entirety.

Magnetic nanoparticles improve the kinetics of forming aggregates 50 compared to a system using micro, or larger, magnetic particles. The magnetic nanoparticles enable separation/enrichment of the diagnostic target bound to the magnetic nanoparticles when the aggregate size is large enough to achieve rapid magnetophoretic separations. This is unlike conventional magnetic enrichment schemes, where a magnetic particle is conjugated to a targeting ligand and forms one side of a "sandwich" immunocomplex.

In one embodiment, the magnetic nanoparticles are of a size and a composition such that a single magnetic nanoparticle will not effect magnetophoretic separation of an aggregate 50. Magnetophoretic separation is only effected using the magnetic nanoparticles when aggregated in aggregates 50 comprising a plurality of magnetic nanoparticles. The aggregates 50 of the invention, therefore, contain a plurality of magnetic nanoparticles, and a plurality of capture conjugates, which then are attached to diagnostic targets, if present in the solution. The plurality of magnetic nanoparticles in the aggregates 50 provides sufficient paramagnetism to enable magnetophoretic separation of the aggregates 50 in the solution.

The magnetophoretic mobility of the aggregates governs the degree to which an aggregate will magnetophorese. The magnetic aggregate separation is influenced by many factors, including the number of individual magnetic particles in an aggregate, magnetic particle size, magnetic field strength, and solution viscosity. The magnetophoretic mobility needs to overcome diffusion before any magnetic separation will occur. For example, if a magnet with 32 MGa maximum energy product is used, the magnetophoretic mobility can overcome diffusion and control the particle movement when the aggregates reach a size of about 50 nm, if iron oxide mNPs are used. Separation speed will improve with increased field strength, if all other characteristics of the system remain the same.

After the aggregates 50 are formed in solution, a magnetic field is applied and the aggregates 50 are immobilized. Immobilized aggregates 50 can be concentrated (e.g., as illustrated in FIG. 1H) and/or washed with a series of solutions to identify any diagnostic target in the aggregates 50. Any technique known to those of skill in the art is useful for identifying the diagnostic target.

As an example of a technique for identifying the diagnostic target, an enzyme/substrate system is used whereby an enzyme is conjugated to a second capture moiety effective in recognizing the diagnostic target of the capture complex. The enzyme is then attached to the diagnostic target in the aggregates via the second capture moiety. A substrate is then added to probe for the presence of the enzyme. A detectable change of the substrate, as examples a change in color, or fluorescence, or light (photon) generation, indicates the presence of the diagnostic target.

Capture Moieties and Target Moieties

The systems and methods disclosed herein include stimuli-responsive capture conjugates that are capable of capturing a diagnostic target from a liquid sample.

As used herein, the term "diagnostic target" refers to a molecule or composition that is indicative of a disease or condition, an indicator of exposure to a toxin, or a therapeutic drug that has been administered to a subject and whose concentration is to be monitored.

In one embodiment, the diagnostic target is a biomarker. Biomarkers can be protein, lipid, carbohydrate, or nucleic acid in nature. For each, the capture moiety has affinity for the target moiety.

Examples of diseases or conditions that may be detected are endocrine, cardiac, and infectious diseases or conditions, and cancer. Suitable biomarkers for each of these are known to those skilled in the art. The scope of the invention also includes the detection of a diagnostic target that is a protein expressed by mammalian or bacterial cells including cells engineered by recombinant techniques, or the detection of mammalian cells, viruses, or bacteria themselves, as is necessary for the assessment of clinical disease including conditions involving the fetus, and for food safety, or assessment of environmental conditions.

Other representative cells useful as a diagnostic target include spores and single-celled organisms (e.g., parasites).

In an exemplary embodiment, the diagnostic target is a CD4 T-cell. The CD4 test measures the amount of CD4 T-cells that are circulating in a subject's blood. The CD4 test is used along with a viral load test to evaluate HIV/AIDS medical conditions. AIDS is diagnosed when a CD4 cell counts drop below 200 cells per microliter of blood. Healthy subjects have a CD4 cell count between 600 and 1,200 cells per microliter of blood. Individuals with a CD4 cell lower than 200 cells per microliter of blood have the greatest risk of developing opportunistic infections. Accordingly, the reagent and methods disclosed herein are useful, in an exemplary embodiment, to capture CD4 T-cells using a capture conjugate capable of binding to CD4 T-cells.

In embodiments of the method of the invention that utilize a second capture moiety to report the presence of the diagnostic target, the diagnostic target is capable of binding to the first and second capture moieties (i.e., is sufficiently large to be subject to a "sandwich" immunoassay).

In certain embodiments, the diagnostic target is an analyte indicative of the presence of a disease or condition, as will be described in more detail below. Representative diseases include infectious diseases such as human immunodeficiency virus (HIV), malaria, dengue, salmonella, rickettsia, influenza, chlamydia, and measles. In a representative embodiment, the infectious disease is present in a subject, and the presence of the infectious disease within the subject body produces antibodies or other biological markers that indicate the presence of the infectious disease in the body. Any of these analytes (antibodies or other biological markers) are diagnostic targets advantageously detected in the present invention. Representative diagnostic targets include a p24 protein of human immunodeficiency virus, a PfHRP2 antigen of malaria, an aldolase antigen of malaria, NS1 antigen of dengue, flagella/somatic/Vi antigens of salmonella, nucleoprotein/hemagglutinin antigens of influenza, LPS antigen of Chlamydia, and antibodies of diseases selected from the group including dengue, salmonella, and rickettsia.

The diagnostic target can be any protein or nucleic acid related to a disease. In one embodiment, the diagnostic target is an antibody against hepatitis B virus. In one embodiment, the diagnostic target is an antibody against hepatitis C virus. In one embodiment, the diagnostic target is an antibody against AIDS virus. In one embodiment, the diagnostic target is the malaria parasitic antigen, or the antiplasmodial antibodies, or the parasitic metabolic products, or the plasmodia nucleic acid fragments. In one embodiment, the diagnostic target is an antibody against tuberculosis bacteria. In one embodiment, the diagnosis target is a dengue fever virus or antibody.

In one embodiment, the diagnostic target is an antibody and the capture moiety is an antigen. In one embodiment, the diagnostic target is an antigen and the capture moiety is an antibody. In one embodiment, the diagnostic target is a nucleic acid oligomer (RNA or DNA) and the capture moiety is a complementary nucleic acid oligomer. In one embodiment, the diagnostic target is a nucleic acid oligomer (an RNA or a DNA) and the capture moiety is a protein. In one embodiment, the diagnostic target is a protein and the capture moiety is a nucleic acid oligomer (RNA or DNA). In one embodiment, the diagnostic target is an enzyme and the capture moiety is a substrate. In one embodiment, the diagnostic target is an enzyme substrate and the capture moiety is an enzyme.

A capture moiety and a diagnostic target form a binding pair. Each has an affinity toward the other (e.g., antigen and antibody). Each of the capture moiety and the diagnostic target can be a variety of different molecules, including peptides, proteins, poly- or oligosaccharides, glycoproteins, lipids and lipoproteins, and nucleic acids, as well as synthetic organic or inorganic molecules having a defined bioactivity, such as an antibiotic or anti-inflammatory agent, that binds to a target site, such as a cell membrane receptor. Exemplary proteins include antibodies (monoclonal, polyclonal, chimeric, single-chain or other recombinant forms), their protein/peptide antigens, protein/peptide hormones, streptavidin, avidin, protein A, protein G, growth factors and their respective receptors, DNA-binding proteins, cell membrane receptors, endosomal membrane receptors, nuclear membrane receptors, neuron receptors, visual receptors, and muscle cell receptors. Exemplary oligonucleotides include DNA (genomic or cDNA), RNA, antisense, ribozymes, and external guide sequences for RNAase P, and can range in size from short oligonucleotide primers up to entire genes. Carbohydrates include tumor associated carbohydrates (e.g., Le$^x$, sialyl Le$^x$, Le$^y$, and others identified as tumor associated as described in U.S. Pat. No. 4,971,905, incorporated herein by reference), carbohydrates associated with cell adhesion receptors (e.g., Phillips et al., *Science* 250:1130-1132, 1990), and other specific carbohydrate binding molecules and mimetics thereof which are specific for cell membrane receptors.

In one embodiment, the capture moiety is an antibody and the diagnostic target is an antigen. In another embodiment, both the capture moiety and the diagnostic target are protein. In another embodiment, the capture moiety is a nucleic acid (DNA or RNA) and the diagnostic target is a complementary nucleic acid (DNA or RNA). In another embodiment, the diagnostic target is a nucleic acid (DNA or RNA) and the capture moiety is a protein. In another embodiment, the capture moiety is a cell membrane receptor and the diagnostic target is a ligand. In another embodiment, the capture moiety is an enzyme and the diagnostic target is a substrate. In another embodiment, the capture moiety is biotin, or a biotin derivative, and the diagnostic target is streptavidin or avidin conjugate of a diagnostic target. In another embodiment, the capture moiety is an avidin (e.g., streptavidin) and the diagnostic target is a biotinylated material effective for binding the diagnostic target.

Among the proteins, streptavidin is particularly useful as a model for other capture moiety-diagnostic target binding pair systems described herein, and also a component useful in many indirect separations and diagnostic technologies, which use the very strong association of the streptavidin-biotin affinity complex. (Wilchek and Bayer, *Avidin-Biotin Technology*, New York, Academic Press, Inc., 1990; and Green, *Meth. Enzymol.* 184:51-67. Protein G, a protein that binds IgG antibodies (Achari et al., *Biochemistry* 31:10449-10457, 1992, and Akerstrom and Bjorck, *J. Biol. Chem.* 261:10240-10247, 1986) is also useful as a model system. Representative immunoaffinity molecules include engineered single chain Fv antibody (Bird et al., *Science* 242:423-426, 1988 and U.S. Pat. No. 4,946,778 to Ladner et al., incorporated herein by reference, Fab, Fab', and monoclonal or polyclonal antibodies.

As used herein, the term "avidin" refers to any biotin-binding protein other than an immunoglobulin that binds biotin including both natural proteins and recombinant and genetically engineered proteins. The term includes the two common biotin-binding proteins known as "egg white" or "avian" avidin and "streptavidin." Egg white or avian avidin, commonly referred to simply as avidin, is a protein that is a constituent of egg white and forms a noncovalent complex with biotin. Streptavidin is a protein isolated from the actinobacterium *Streptomyces avidinii* and also forms a noncovalent complex with biotin. Other bacterial sources of biotin binding proteins are also known. Both egg white avidin and streptavidin are tetrameric proteins in which the biotin binding sites are arranged in pairs on opposite faces of the avidin molecule. The term also refers to avidin derivatives including succinyl avidin, ferritin avidin, enzyme avidin, and crosslinked avidin. The term "biotin" refers to any one of a variety of biotin derivatives and analogs that are effective in avidin binding. Suitable biotin moieties include those moieties that enable the biotinylated peptide fragment to be isolated by avidin and related avidin proteins. Representative biotin moieties include biotin derivatives such as iminobiotin, biocytin, and caproylamidobiotin, and biotin analogs such as desthiobiotin and biotin sulfone.

Other binding pairs include concanavalin A and other lectins known to those skilled in the art, which have affinity for specific sugars (e.g., mannose, glucose, and galactose).

Stimuli-Responsive Polymers

A central feature of the present invention is the use of "stimuli-responsive polymers". As used herein, the term "stimuli-responsive polymers" refers to a class of polymers (or polymer moieties) that exhibit a change from a hydrophobic state to a hydrophilic state as the result of an environmental stimulus.

As noted above, each of the magnetic particle and the non-magnetic particle bears a stimuli-responsive polymer. The presence of the stimuli-responsive polymer provides for the formation of the aggregate on the application of an appropriate stimulus. For example, when the magnetic and non-magnetic particles bear a thermally-responsive polymer, the aggregate is formed by heating the liquid to a temperature above the lower critical solution temperature of the thermally-responsive polymer (e.g., a polymer comprising N-isopropylacrylamide repeating units, an N-isopropylacrylamide polymer or copolymer). When the magnetic and non-magnetic particles bear a pH-responsive polymer, the aggregate is formed by adjusting the pH of the liquid to a pH that causes the polymers to become associative (e.g., a polymer comprising acrylic acid or alkylacrylic acid repeating units, an acrylic acid or alkylacrylic acid polymer or copolymer). A representative pH-responsive polymer is an N-isopropylacrylamide/methylacrylic acid/tert-butyl methacrylate copolymer such as poly(N-isopropylacrylamide-co-methylacrylic acid-co-tert-butyl methacrylate. When the magnetic and non-magnetic particles bear an ionic strength-responsive polymer, the aggregate is formed by adjusting the ionic strength of the liquid such that the polymers become associative. Similarly, when the magnetic and non-magnetic particles bear a light-responsive polymer, the aggregate is formed by irradiating the liquid with a wavelength of light effective to cause the polymers to become associative.

An effective stimulus to the stimuli-responsive polymer is one that changes the degree to which the stimuli-responsive polymer is hydrophilic, and, relatedly, the degree to which the stimuli-responsive polymer is hydrophobic. Such an effective stimulus is typically caused by the chemical makeup of the stimuli-responsive polymer, as described in more detail below.

Two representative stimuli-responsive polymers useful in the present invention are temperature-responsive polymers and pH-responsive polymers. As used herein, the term "temperature-responsive polymer" refers to polymers that are reversibly self-associative in response to temperature. Particularly, above a lower critical solution temperature (LCST), temperature-responsive polymers are self-associative, meaning the polymers bind to themselves and other similar temperature-responsive polymers. Below the LCST, the polymer is hydrophilic and highly solvated, while above the LCST, it is aggregated and phase separated. Of use in the present invention is the sharp transition from individual chains to the aggregated state over a very narrow temperature range of a few degrees. The change is completely reversible, and reversal of the stimulus results in the polymer going back into solution rapidly.

Similarly, pH-responsive polymers transition from hydrophobic to hydrophilic based on a critical pH. PH-responsive polymers are known to those of skill in the art, and are described in the context of affinity binding in U.S. Pat. No. 7,625,764, incorporated herein by reference in its entirety. Representative pH-responsive polymers include polymers formed from monomers that include acrylic acid, methacrylic acid, propyl acrylic acid, butyl acrylate, butyl methacrylate, and alkyl-substituted acrylic acids in general.

Other responsive polymers are known to those of skill in the art, for example light-sensitive polymers. Any polymer capable of forming aggregates, as disclosed herein, is useful in the present invention.

The present invention is primarily disclosed in terms of temperature-responsive polymers. However, it will be appreciated by those of skill in the art that pH-responsive polymers, or other stimuli-responsive polymers, can be substituted for temperature-responsive polymers in the methods and devices disclosed herein. Additionally, some polymers are both temperature- and pH-responsive.

Therefore, certain methods and devices of the invention include the use of both temperature and pH to aggregate polymers.

The stimuli-responsive polymers coupled to the magnetic nanoparticles and capture moieties can be either the same or different in composition (i.e., species of polymer) and type (i.e., the stimulus the polymer responds to), as long as aggregation between the magnetic nanoparticles and capture moieties can be effectively induced by one or more stimuli.

Temperature-responsive polymers are known to those of skill in the art, with the most common being poly(N-isopropylacrylamide) (PNIPAAm). Other temperature-responsive polymers include those formed from monomers including dimethylaminoethyl acrylamide, ethylene oxide, and elastin-like polypeptide.

As set forth in U.S. Pat. No. 7,625,764, incorporated herein by reference in its entirety, temperature-responsive polymers can be used to bind two or more distinct objects (e.g., particles, molecules, etc.) through the self-associative interaction of temperature-responsive polymer moieties attached to each object in a solution above the LCST.

The presence of the stimuli-responsive polymer moiety on a conjugate provides for the formation of the aggregate on the application of an appropriate stimulus. For example, when the conjugates bear a thermally-responsive polymer, the aggregate is formed by heating the liquid to a temperature above the lower critical solution temperature of the thermally-responsive polymer (e.g., a polymer comprising N-isopropylacrylamide repeating units, an N-isopropylacrylamide polymer or copolymer). When the conjugates bear a pH-responsive polymer, the aggregate is formed by adjusting the pH of the liquid to a pH that causes the polymers to become associative (e.g., a polymer comprising acrylic acid or alkylacrylic acid repeating units, an acrylic acid or alkylacrylic acid polymer or copolymer). A representative pH-responsive polymer is an N-isopropylacrylamide/methylacrylic acid/tert-butyl methacrylate copolymer such as poly(N-isopropylacrylamide-co-methylacrylic acid-co-tert-butyl methacrylate. When the conjugates bear an ionic strength-responsive polymer, the aggregate is formed by adjusting the ionic strength of the liquid such that the polymers become associative. Similarly, when the conjugates bear a light-responsive polymer, the aggregate is formed by irradiating the liquid with a wavelength of light effective to cause the polymers to become associative.

The stimuli-responsive polymer can be any polymer having a stimuli-responsive property. The stimuli-responsive polymer can be any one of a variety of polymers that change their associative properties (e.g., change from hydrophilic to hydrophobic) in response to a stimulus. The stimuli-responsive polymer responds to changes in external stimuli such as the temperature, pH, light, photo-irradiation, exposure to an electric field, ionic strength, and the concentration of certain chemicals by exhibiting property change. For example, a thermally-responsive polymer is responsive to changes in temperature by exhibiting a LCST in aqueous solution. The stimuli-responsive polymer can be a multi-responsive polymer, where the polymer exhibits property change in response to combined simultaneous or sequential changes in two or more external stimuli.

The stimuli-responsive polymers may be synthetic or natural polymers that exhibit reversible conformational or physiochemical changes such as folding/unfolding transitions, reversible precipitation behavior, or other conformational changes to in response to stimuli, such as to changes in temperature, light, pH, ions, or pressure. Representative stimuli-responsive polymers include temperature-sensitive polymers (also referred to herein as "temperature-responsive polymers" or "thermally-responsive polymers"), pH-sensitive polymers (also referred to herein as "pH-responsive polymers"), and light-sensitive polymers (also referred to herein as "light-responsive polymers").

Stimuli-responsive polymers useful in making the particles described herein can be any, which are sensitive to a stimulus that causes significant conformational changes in the polymer. Illustrative polymers described herein include temperature-, pH-, ion- and/or light-sensitive polymers. Hoffman, A. S., "Intelligent Polymers in Medicine and Biotechnology", *Artif. Organs.* 19:458-467, 1995; Chen, G. H. and A. S. Hoffman, "A New Temperature- and Ph-Responsive Copolymer for Possible Use in Protein Conjugation", *Macromol. Chem. Phys.* 196:1251-1259. 1995; Irie, M. and D. Kungwatchakun, "Photoresponsive Polymers. Mechanochemistry of Polyacrylamide Gels Having Triphenylmethane Leuco Derivatives", *Makromol. Chem., Rapid Commun.* 5:829-832, 1985; and Irie, M., "Light-induced Reversible Conformational Changes of Polymers in Solution and Gel Phase", *ACS Polym. Preprints,* 27(2):342-343, 1986; which are incorporated by reference herein.

Representative stimuli-responsive oligomers and polymers useful in the embodiments described herein can be synthesized that range in molecular weight from about 1,000 to 100,000 Daltons. In one embodiment, these syntheses are based on the chain transfer-initiated free radical polymerization of vinyl-type monomers, as described herein, and by (1) Tanaka, T., "Gels", *Sci. Amer.* 244:124-138. 1981; (2) Osada, Y. and S. B. Ross-Murphy, "Intelligent Gels", *Sci. Amer,* 268:82-87, 1993; (3) Hoffman, A. S., "Intelligent Polymers in Medicine and Biotechnology", *Artif. Organs* 19:458-467, 1995; also *Macromol. Symp.* 98:645-664, 1995; (4) Feijen, J., et al., "Thermosensitive Polymers and Hydrogels Based on N-isopropylacrylamide", 11*th European Conf. on Biomtls:* 256-260, 1994; (5) Monji, N. and A. S. Hoffman, "A Novel Immunoassay System and Bioseparation Process Based on Thermal Phase Separating Polymers", *Appl. Biochem. and Biotech.* 14:107-120, 1987; (6) Fujimura, M., T. Mori and T. Tosa, "Preparation and Properties of Soluble-Insoluble Immobilized Proteases", *Biotech. Bioeng.* 29:747-752, 1987; (7) Nguyen, A. L. and J. H. T. Luong, "Synthesis and Applications of Water-Soluble Reactive Polymers for Purification and Immobilization of Biomolecules", *Biotech. Bioeng.* 34:1186-1190, 1989; (8) Taniguchi, M., et al., "Properties of a Reversible Soluble-Insoluble Cellulase and Its Application to Repeated Hydrolysis of Crystalline Cellulose", *Biotech. Bioeng.* 34:1092-1097, 1989; (9) Monji, N., et al., "Application of a Thermally-Reversible Polymer-Antibody Conjugate in a Novel Membrane-Based Immunoassay", *Biochem. and Biophys. Res. Comm.* 172:652-660, 1990; (10) Monji, N. C. A. Cole, and A. S. Hoffman, "Activated, N-Substituted Acrylamide Polymers for Antibody Coupling: Application to a Novel Membrane-Based Immunoassay", *J. Biomtls. Sci. Polymer Ed.* 5:407-420, 1994; (11) Chen, J. P. and A. S. Hoffman, "Polymer-Protein Conjugates: Affinity Precipitation of Human IgG by Poly(N-Isopropyl Acrylamide)-Protein A Conjugates", *Biomtls.* 11:631-634, 1990; (12) Park, T. G. and A. S. Hoffman, "Synthesis and Characterization of a Soluble, Temperature-Sensitive Polymer-Conjugated Enzyme, *J. Biomtls. Sci. Polymer Ed.* 4:493-504, 1993; (13) Chen, G. H., and A. S. Hoffman, Preparation and Properties of Thermo-Reversible, Phase-Separating Enzyme-Oligo (NIPAAm) Conjugates", *Bioconj. Chem.* 4:509-514, 1993; (14) Ding, Z. L., et al., "Synthesis and Purification of Thermally-Sensitive Oligomer-Enzyme Conjugates of Poly (NIPAAm)-Trypsin", *Bioconj. Chem.* 7: 121-125, 1995; (15) Chen, G. H. and A. S. Hoffman, "A New Temperature- and pH-Responsive Copolymer for Possible Use in Protein Conjugation", *Macromol. Chem. Phys.* 196:1251-1259, 1995; (16) Takei, Y. G., et al., "Temperature-responsive Bioconjugates. 1. Synthesis of Temperature-Responsive Oligomers with Reactive End Groups and their Coupling to Biomolecules", *Bioconj. Chem.* 4:42-46, 1993; (17) Takei, Y. G., et al., "Temperature-responsive Bioconjugates. 2. Molecular Design for Temperature-modulated Bioseparations", *Bioconj. Chem.* 4:341-346, 1993; (18) Takei, Y. G., et al., "Temperature-responsive Bioconjugates. 3. Antibody-Poly(N-isopropylacrylamide) Conjugates for Temperature-Modulated Precipitations and Affinity Bioseparations", *Bioconj. Chem.* 5:577-582, 1994; (19) Matsukata, M., et al., "Temperature Modulated Solubility-Activity Alterations for Poly(N-Isopropylacrylamide)-Lipase Conjugates", *J. Biochem.* 116:682-686, 1994; (20) Chilkoti, A., et al., "Site-Specific Conjugation of a Temperature-Sensitive Polymer to a Genetically-Engineered Protein", *Bioconj. Chem.* 5:504-507, 1994; and (21) Stayton, P. S., et al., "Control of Protein-Ligand Recognition Using a Stimuli-Responsive Polymer", *Nature* 378:472-474, 1995.

The stimuli-responsive polymers useful herein include homopolymers and copolymers having stimuli-responsive behavior. Other suitable stimuli-responsive polymers include block and graft copolymers having one or more stimuli-responsive polymer components. A suitable stimuli-responsive block copolymer may include, for example, a temperature-sensitive polymer block, or a pH-sensitive block. A suitable stimuli-responsive graft copolymer may include, for example, a pH-sensitive polymer backbone and pendant temperature-sensitive polymer components, or a temperature-sensitive polymer backbone and pendant pH-sensitive polymer components.

The stimuli-responsive polymer can include a polymer having a balance of hydrophilic and hydrophobic groups, such as polymers and copolymers of N-isopropylacrylamide. An appropriate hydrophilic/hydrophobic balance in a smart vinyl type polymer is achieved, for example, with a pendant hydrophobic group of about 2-6 carbons that hydrophobically bond with water, and a pendant polar group such as an amide, acid, amine, or hydroxyl group that H-bond with water. Other polar groups include sulfonate, sulfate, phosphate, and ammonium ionic groups. Preferred embodiments are for 3-4 carbons (e.g., propyl, isopropyl, n-butyl, isobutyl, and t-butyl) combined with an amide group (e.g. PNIPAAm), or 2-4 carbons (e.g., ethyl, propyl, isopropyl, n-butyl, isobutyl, and t-butyl) combined with a carboxylic acid group (e.g., PPAA). There is also a family of smart A-B-A (also A-B-C) block copolymers of polyethers, such as PLURONIC polymers having compositions of PEO-PPO-PEO, or polyester-ether compositions such as PLGA-PEG-PLGA. In one embodiment, the stimuli-responsive polymer is a temperature responsive polymer, poly(N-isopropylacrylamide) (PNIPAAm).

The stimuli-responsive polymer useful in the invention can be a smart polymer having different or multiple stimuli responsivities, such as homopolymers responsive to pH or light. Block, graft, or random copolymers with dual sensitivities, such as pH and temperature, light and temperature, or pH and light, may also be used.

Illustrative embodiments of the many different types of thermally-responsive polymers that may be conjugated to interactive molecules are polymers and copolymers of N-isopropyl acrylamide (NIPAAm). PolyNIPAAm is a thermally-responsive polymer that precipitates out of water at 32° C., which is its lower critical solution temperature (LCST), or cloud point (Heskins and Guillet, *J. Macromol. Sci.-Chem. A*2:1441-1455, 1968). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551-2570, 1975; Priest et al., *ACS Symposium Series* 350:255-264, 1987; and Heskins and Guillet, *J. Macromol. Sci.-Chem.* A2:1441-1455, 1968, the disclosures of which are incorporated herein). Copolymers can be produced having higher or lower LCSTs and a broader temperature range of precipitation.

Thermally-responsive oligopeptides also may be incorporated into the conjugates.

Synthetic pH-responsive polymers useful in making the conjugates described herein are typically based on pH-sensitive vinyl monomers, such as acrylic acid (AAc), methacrylic acid (MAAc) and other alkyl-substituted acrylic acids such as ethylacrylic acid (EAAc), propylacrylic acid (PAAc), and butylacrylic acid (BAAc), maleic anhydride (MAnh), maleic acid (MAc), AMPS (2-acrylamido-2-methyl-1-propanesulfonic acid), N-vinyl formamide (NVA), N-vinyl acetamide (NVA) (the last two may be hydrolyzed to polyvinylamine after polymerization), aminoethyl methacrylate (AEMA), phosphoryl ethyl acrylate (PEA) or methacrylate (PEMA). pH-Responsive polymers may also be synthesized as polypeptides from amino acids (e.g., polylysine or polyglutamic acid) or derived from naturally-occurring polymers such as proteins (e.g., lysozyme, albumin, casein), or polysaccharides (e.g., alginic acid, hyaluronic acid, carrageenan, chitosan, carboxymethyl cellulose) or nucleic acids, such as DNA. pH-Responsive polymers usually contain pendant pH-sensitive groups such as $-OPO(OH)_2$, $-COOH$, or $-NH_2$ groups. With pH-responsive polymers, small changes in pH can stimulate phase-separation, similar to the effect of temperature on solutions of PNIPAAm (Fujimura et al. *Biotech. Bioeng.* 29:747-752 (1987)). By randomly copolymerizing a thermally-sensitive NIPAAm with a small amount (e.g., less than 10 mole percent) of a pH-sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH-sensitive groups are ionized. When the pH-sensitive monomer is present in a higher content, the LCST response of the temperature-sensitive component may be "eliminated" (e.g., no phase separation seen up to and above 100° C.).

Graft and block copolymers of pH and temperature-sensitive monomers can be synthesized that retain both pH and temperature transitions independently. Chen, G. H., and A. S. Hoffman, *Nature* 373:49-52, 1995. For example, a block copolymer having a pH-sensitive block (polyacrylic acid) and a temperature-sensitive block (PNIPAAm) can be useful in the invention.

Light-responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state.

In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature) responsive polymer. A number of protocols for such dye-conjugated monomer syntheses are known.

Although both pendant and main chain light sensitive polymers may be synthesized and are useful for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Light-sensitive compounds may be dye molecules that isomerize or become ionized when they absorb certain wavelengths of light, converting them from hydrophobic to hydrophilic conformations, or they may be other dye molecules, which give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes (Ciardelli, *Biopolymers* 23:1423-1437, 1984; Kungwatchakun and Irie, *Makromol. Chem., Rapid Commun.* 9:243-246, 1988; Lohmann and Petrak, *CRC Crit. Rev. Therap. Drug Carrier Systems* 5:263, 1989; Mamada et al., *Macromolecules* 23:1517, 1990, each of which is incorporated herein by reference). When this type of dye is exposed to 350-410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant dye to a hydrophilic or hydrophobic state can also cause individual chains to expand or contract their conformations. When the polymer main chain contains light sensitive groups (e.g., azo benzene dye) the light-stimulated state may actually contract and become more hydrophilic upon light-induced isomerization. The light-sensitive polymers can include polymers having pendant or backbone azobenzene groups.

Polysaccharides, such as carrageenan, that change their conformation, for example, from a random to an ordered conformation, as a function of exposure to specific ions, such as potassium or calcium, can also be used as the stimuli-responsive polymers. In another example, a solution of sodium alginate may be gelled by exposure to calcium. Other specific ion-sensitive polymers include polymers with pendant ion chelating groups, such as histidine or EDTA.

Polymers that are responsive to changes in ionic strength can also be used.

Antibody-Antigen Assay

FIGS. 2A through 2F illustrate an exemplary embodiment wherein the aggregates comprise an antigen diagnostic target 115.

Figure 2A:
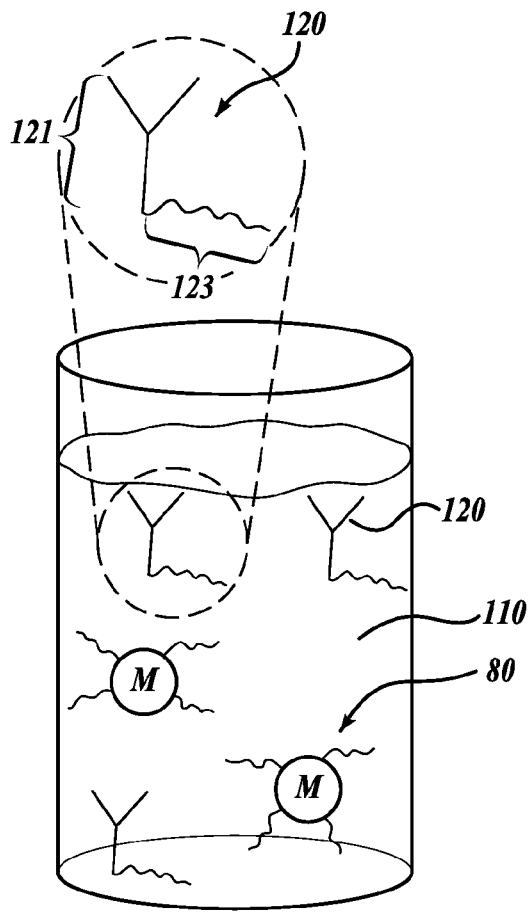
FIGS. 2A-2F are diagrammatic illustrations of an exemplary method for immobilizing an antigen diagnostic target from a solution comprising temperature-responsive magnetic nanoparticles and antibody conjugates in accordance with the embodiments provided herein.

Referring to FIG. 2A, a smart regent solution 110 is provided comprising capture conjugates 120, each of which comprise a first capture moiety 121 (illustrated as an antibody) and a temperature-responsive polymer moiety 123.

The solution 110 further comprises magnetic particles 80, similar to those described with regard to FIG. 1A-1H.

Figure 2B:
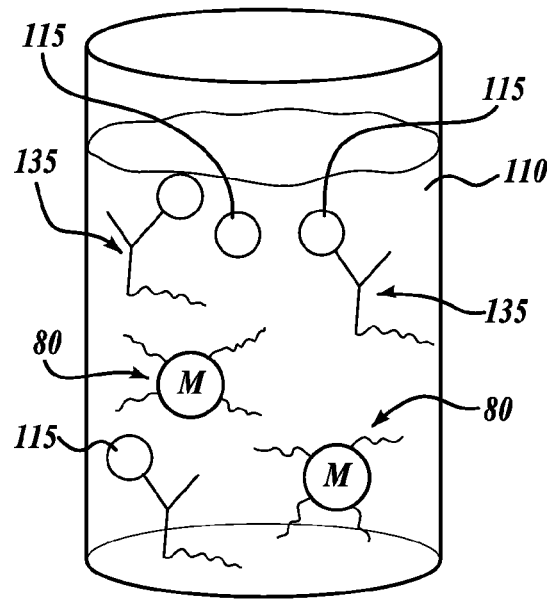

Referring to FIG. 2B, the antigen diagnostic target 115 is bound to a capture conjugate 120. The capture conjugates 120 bind (e.g., spontaneously) to the diagnostic targets 115 to form capture complexes 135.

The first capture moiety 121 is, therefore, defined as a moiety having a binding affinity to the diagnostic target 115. Depending on the composition of the diagnostic target 115, the first capture moiety 121 may be an antibody, an antigen, or other chemical functional group having a binding affinity to the diagnostic target 151.

The first capture moiety 121 can also be part of a serology system whereby the capture conjugate 120 may comprise three or more moieties to provide binding to an anti-[disease] antibody. In such an embodiment, the capture conjugate 120 comprises the temperature-responsive polymer moiety 123, and a first capture moiety 121 comprising an anti-[disease] antigen antibody bound to a disease antigen via the antibody. The antigen on the first capture moiety 121 then provides binding to the anti-[disease] antibody, which is the diagnostic target 115.

The temperature-responsive polymer moiety 123 is bound to the first capture moiety 121 so as to form the capture conjugate 120. The temperature-responsive polymer moiety is self-associative in response to temperature change greater than the LCST, as has been described previously. Representative temperature-responsive polymer moieties are pNIPAAm moieties.

The capture conjugate 120 (and further conjugates, such as the reporting conjugate and the magnetic particles described herein) can be in a dried form and added to the biological fluid 110 or solvated in a solution added to the biological fluid 110. One advantage of the use of dried capture conjugate 120 is to avoid the need for refrigeration of a solution containing solvated capture conjugate 120.

Figure 2C:
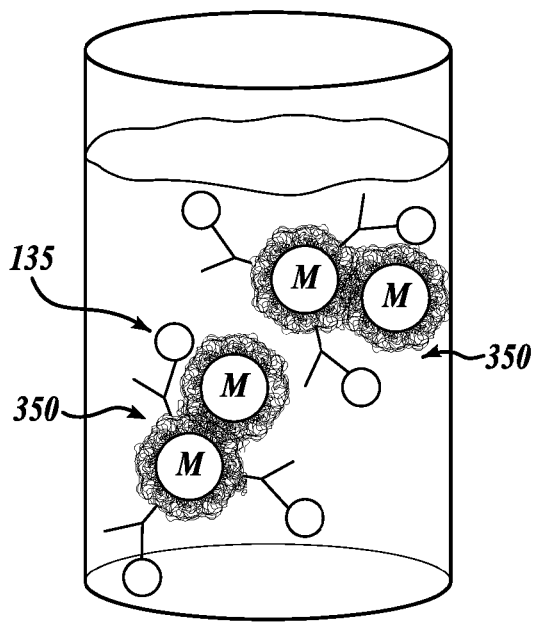

Aggregates 350 of the capture complex 135 are formed, with reference to FIG. 2C, for example, by providing the capture complexes 135 heated above the LCST of the temperature-responsive polymer moieties on each of the capture conjugates 120 and smart mNPs 80. This rise in temperature above the LCST causes the temperature-responsive polymer moieties to become self-associative so as to form aggregates 350 comprising a plurality of capture complexes 135 bound together with smart mNPs 80 through the associative binding between temperature-responsive polymer moieties on each.

Figure 2D:
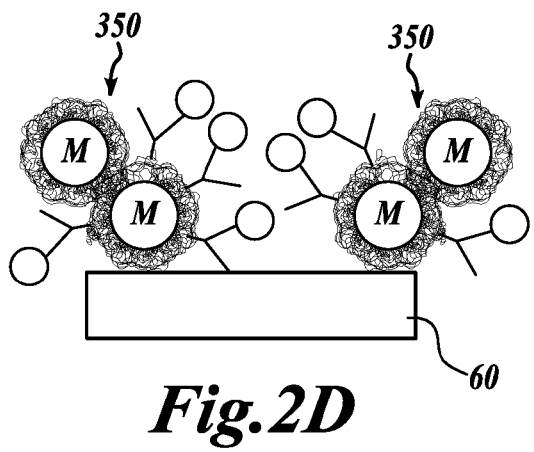

In the present invention, the immobilization of the diagnostic target 115 is accomplished in one embodiment by first aggregating the aggregates 350. The solution 110 is then pushed through a membrane 60 (e.g., filter) having a surface chemistry that adheres the aggregates 350 to membrane 60 upon contact. As illustrated in FIG. 2D, the membrane 60 collects the aggregates 350 from solution after the solution is passed through the filter 60. The aggregates 350 are immobilized on the surface of the membrane 60.

Regarding immobilization of the aggregates 350 on the membrane 60, any mechanism for immobilization can be implemented in the present invention. Particularly useful are chemical adhesion means. Representative chemical adhesion means include hydrogen bonding between at least one moiety on the aggregate 350 and the membrane 60; and hydrophobic-hydrophobic (or hydrophilic-hydrophilic) associative binding. Associative binding can be between the aggregate 350 and an untreated membrane (e.g., hydroxylated nylon) or a membrane having temperature-responsive moieties attached thereto.

After immobilization, the aggregates 350 can be further processed to identify the diagnostic targets 115 using methods known to those of skill in the art. For example, the aggregates 350 can be washed with a solution, or series of solutions, containing the reagents to perform visual indication of the presence of the diagnostic target 115, such as an enzyme-based visual indicator or using a gold particle-based visual indicator known to those of skill in the art. Alternatively, the immobilized aggregates 350 can be re-solvated in a relatively small amount of solvent and tested by lateral flow or other techniques known to those of skill in the art.

Figure 2E:
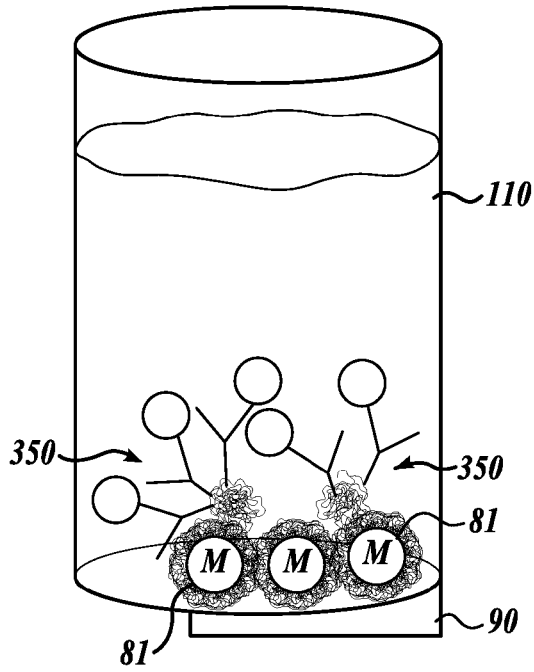
Figure 2F:
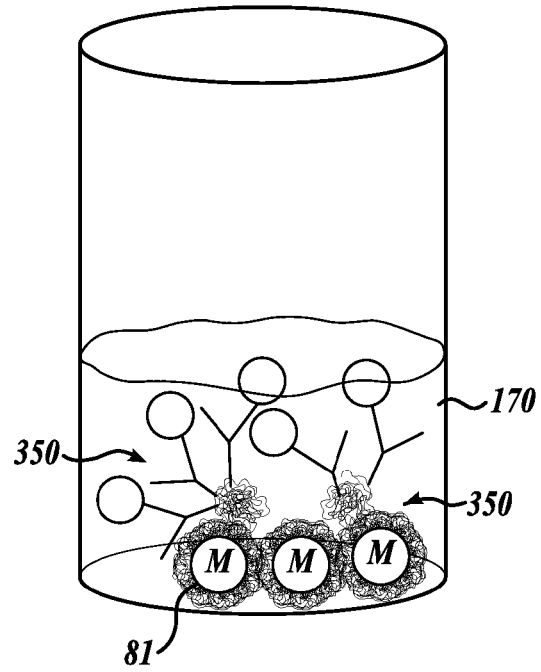

As illustrated in FIG. 2E, a magnet 90 can be used to immobilize the aggregates 350 in a magnetic field so as to concentrate the aggregates 350 in the biological fluid 310. Then, using techniques known to those of skill in the art, the supernatant of the solution above the liquid level of the aggregates 350 can be removed to provide a concentrated solution 170, as illustrated in FIG. 2F, that contains all of the aggregates 350 previously in the larger volume of the solution 110. By increasing the concentration of the aggregates 350, the concentrated solution 170 can then be further processed, for example, by lateral flow methods to provide a stronger signal for detection of the diagnostic target 115 compared to a more dilute solution without co-aggregation and isolation.

Aggregates Comprising Reporting Moieties

Referring to FIGS. 3A through 3C, a series of diagrammatic illustrations similar to aspects of FIGS. 1A through 2F are presented. Similar to FIGS. 1A through 2F, the purpose of the steps illustrated in FIGS. 3A through 3C is to immobilize a diagnostic target 115 for identification. However, in the embodiments illustrated in FIGS. 3A through 3C, a detector moiety 243 (e.g., a visual indicator) is incorporated into the process.

Referring to FIG. 3A, a solution 210 is provided comprising a biological fluid, the diagnostic target 115, a capture conjugate 120 comprising a first binding moiety and a temperature-responsive polymer moiety, a smart mNP 80, and a detector conjugate 240 comprising a second binding moiety 241 and a reporting moiety 243.

Regarding the reporting conjugate 240, the second binding moiety 241 has a binding affinity to the diagnostic target 115 such that the second binding moiety 241 will bind to the diagnostic target 115 when in close proximity in solution. The second binding moiety 241 can be any binding moiety capable of binding to the diagnostic target 115, similar to the first binding moiety described above.

The detector moiety 243 is a moiety that assists in reporting the presence of the diagnostic target 115. In one embodiment, the reporting moiety is selected from the group consisting of a metallic particle and a reporting enzyme. In one embodiment, the metallic particle is a gold particle. Gold particles are useful in visually identifying diagnostic targets 115 in the present invention because a sufficient concentration of gold particles will produce a color identifiable to human or mechanical vision so as to provide a simple, positive identification of a diagnostic target 115 attached to a gold particle.

Additional reporting moieties include luminescent moieties, as are known to those of skill in the art.

Reporting enzymes are also useful as a reporting moiety. The use of enzymes for visual identification is well known to those of skill in the art, such as in enzyme-linked immunosorbent assay (ELISA) techniques. If a reporting enzyme is the detector moiety 243 on the detector conjugate 240, the reporting enzyme can be later processed so as to contact a substrate to the enzyme, wherein the substrate produces, for example, a color change detectable by human or mechanical vision.

Referring to FIG. 3B, the detector conjugates 240 and capture conjugates 120 both bind to the diagnostic target 115 to form a capture complex 235.

Referring to FIG. 3C, a plurality of capture complexes 235, along with smart mNPs 80 aggregate after an effective stimulus is applied to the solution 210 (e.g., a temperature above the LCST of the temperature-responsive polymer moieties is provided). The resulting aggregates 250 comprise a plurality of capture complexes 235, each capture complex comprising at least one diagnostic target 115 and at least one detector moiety 243.

Similar to the description above with reference to FIGS. 1F-1H, the aggregates 250 can be immobilized, concentrated, or otherwise isolated to aid in analysis. Typically the aggregates 250 are washed, or other measures are taken to remove unbound detector conjugates 240. After excess detector conjugate 240 is removed, any detected detector moieties 243 is attached to a diagnostic target 115. The detector moieties 243 typically provide, for example, a visual indication of the presence of the diagnostic target 115. That is, if a color appears, that color is definitively the result of a large number of aggregates 250, each containing at least one detector moiety 243 and one diagnostic target 115. Therefore, the detectable color change can be positively stated as being attributable to the presence of the diagnostic target 115 in the solution.

It will be appreciated by those of skill in the art that additional processing steps may be required after the aggregates 250 are immobilized from the solution. For example, additional reagents may be passed over the aggregates 250 so as to effect color change if an enzyme is used.

Multiple-Diagnostic Targets

While the embodiments disclosed herein have been described with reference to a single diagnostic target, it will be appreciated that the methods can be modified to test for multiple diagnostic targets.

For example, in certain embodiments, first capture conjugates and second capture conjugates are provided in a solution, wherein the first capture conjugates will bind to a first diagnostic target and the second capture conjugates will bind to a second diagnostic target. When the capture conjugates are combined with smart MNPs in a biological solution, any of the first and second diagnostic targets in the solution will be bound to the respective capture conjugate to form capture complexes. The capture complexes are then aggregated with the smart MNPs to form aggregates that are isolated or otherwise tested to detect the first and second diagnostic targets.

The number of diagnostic targets for which the provided embodiments are capable of isolating is limited only by the compatibility of the components of the assay (e.g., non-specific binding or immiscibility).

As an example, U.S. Patent Application Publication No. 2011/0003392, the disclosure of which is incorporated herein by reference in its entirety, demonstrates the viability of capturing multiple types of diagnostic targets from a single solution using two different types of capture moieties.

Separation Efficiency of Aggregates

Experimental results indicate that the magnetic separation of aggregates is at least 90% effective in concentrating aggregates from a bulk solution.

Temperature-responsive mNPs and anti-p24 conjugates were both functionalized with NIPAM according to known methods. The anti-p24 conjugates were fluorescently labeled. The temperature-responsive mNPs and anti-p24 conjugates were mixed in PBS (pH 7.4) at room temperature, and then incubated at 45° C. for 10 minutes to form aggregates. After the aggregation, the solution was incubated at 45° C. for an additional 2 minutes with an applied magnetic field for capturing the aggregates.

The separation efficiency (i.e., how well the components were removed from the bulk solution and concentrated adjacent the magnet) was determined separately for the mNPs and the capture conjugates.

Figure 4:
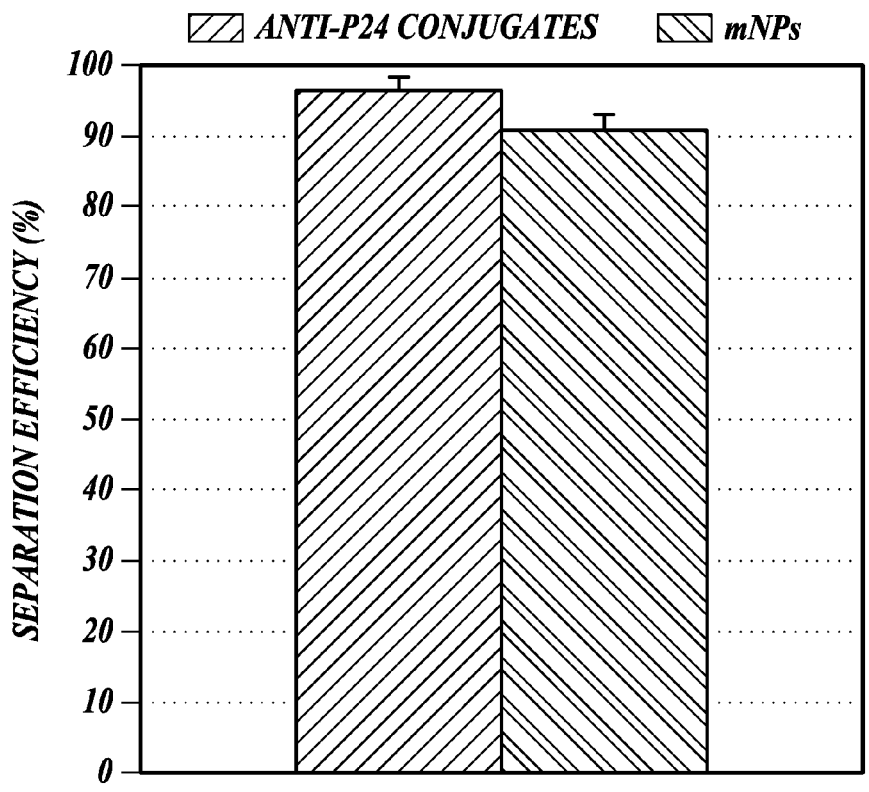
FIG. 4 graphically illustrates the efficiency of separating aggregates comprising stimuli-responsive magnetic nanoparticles and antibody conjugates in accordance with the embodiments provided herein.

The mNPs absorb light at 400 nm but the fluorescently labeled anti-p24 conjugates are transparent. This optical distinction between the two components is used to measure the separation efficiency of smart mNPs in the solution. The solution absorbance reduction was measured before and after application of the magnetic field to aggregates at 400 nm to determine the smart mNP separation efficiency. As illustrated in FIG. 4, the absorbance data show the smart mNP separation efficiency is ca. 90%.

Additionally, the solution's fluorescent intensity before and after the separation is used determined the anti-p24 conjugate separation efficiency.

Antibody (Ab) Capture Conjugates: p24 Antibodies

In certain embodiments, the capture conjugate is an antibody conjugate. In an exemplary embodiment, the antibody conjugate is a p24 antibody.

Sample solutions containing 10% serum, 2 mg/mL pNIPAAm-functionalized mNPs, and 100 pg/mL of p24 were prepared. Various volumes of pNIPAAm-Ab conjugate were added to these solutions and allowed 30 minutes incubation at room temp. After 5 minutes of heating (ca. 45° C.) to aggregate the pNIPAAm mNPs and Ab conjugates, a magnetic field of 13.2 KGs was applied to the heated solution for 2 minutes to achieve magnetic separation.

Figure 5:
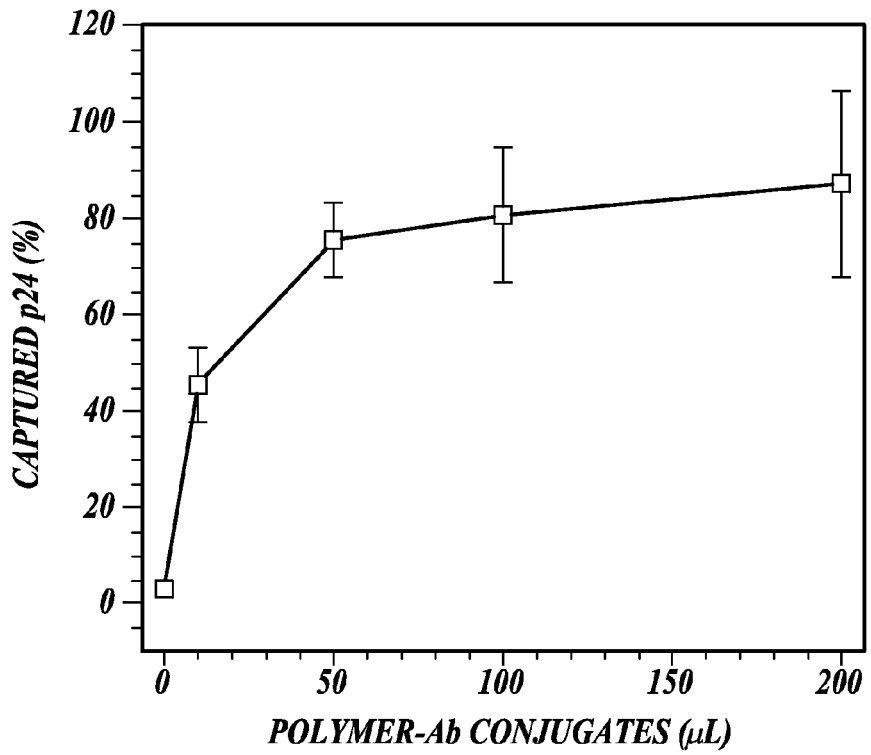
FIG. 5 graphically illustrates the relationship between stimuli-responsive antibody conjugates and the percentage of diagnostic target captured by the conjugates in accordance with the embodiments provided herein.

The amount of p24 collected in the supernatant was measured using enzyme-linked immunosorbent assay (ELISA) to determine the amount of unbound p24 in the solution. FIG. 5 graphically illustrates the increase of p24 separation efficiency when the amount of Ab conjugates increases. Accordingly, the smart solvent system provided herein is effective in capturing targets such as the p24 protein of HIV.

Figure 6:
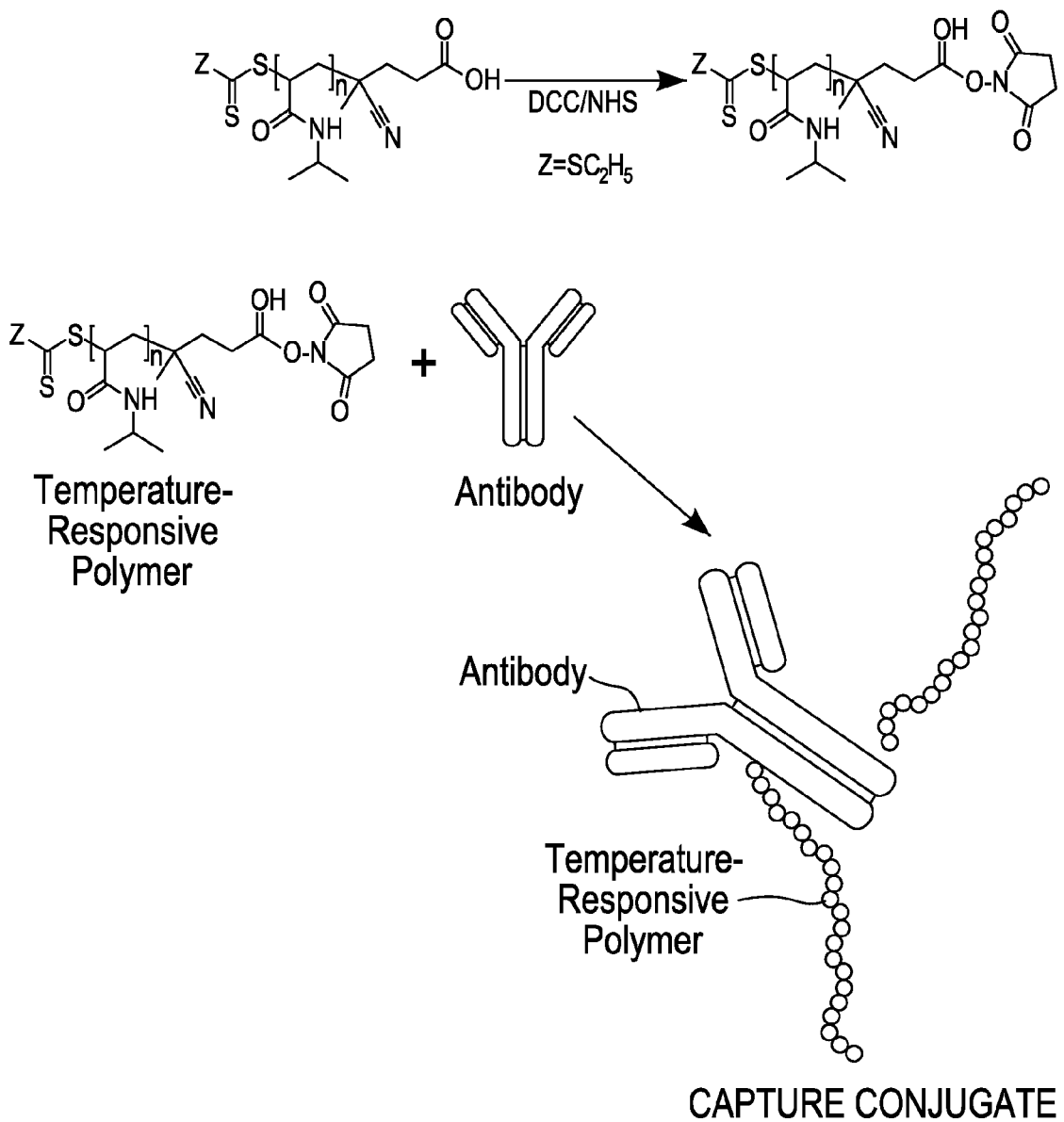
FIG. 6 illustrates a reaction scheme for conjugating a temperature-responsive polymer moiety to an antibody to form a capture conjugate in accordance with the embodiments provided herein.

The synthesis of p24 Ab conjugates will now be described. As illustrated in FIG. 6, a capture conjugate was synthesized from an antibody and the temperature-responsive polymer PNIPAAm. Initially, the carboxylate chain end on the PNIPAAm polymer chain was "activated" using DCC/NHS. The "activated" polymer chains were then conjugated to the amine functional group on the antibody to form the capture complex having the antibody and a temperature-responsive polymer moiety. The PNIPAAm chains were synthesized using reversible addition-fragmentation chain transfer polymerization (RAFT) and contain a carboxylate chain end, which was used to covalently conjugate to the amine functional groups on the p24 antibodies via carbodiimide chemistry (e.g., DCC/NHS), as is known to those of skill in the art.

The carboxylate was activated (FIG. 6) in methylene chloride by mixing pNIPAAm:DCC:NHS at 1:1.1:1.1 ratio. The activation was allowed to proceed overnight at room temperature. The resulting activated polymer, NHS-pNIPAAm, was collected by precipitating in n-hexane. For conjugation, the NHS-pNIPAAm was pre-dissolved in anhydrous DMSO and added into p24 antibody solution (pH 8.5). The resulting reaction mixture contained 10% DMSO. The reaction was allowed to proceed overnight at 4° C. and then a desalting column was used to remove small molecule impurities. Capture conjugates, which exhibit temperature-responsiveness, were collected via centrifugation (10000 RPM, 5 minutes) at 40° C. The unmodified antibodies in the supernatant were discarded.

Capture conjugates were made using monoclonal p24 antibodies from commercially available sources, such as Maine Biotechnology Services (MBS), ImmunoDiagnostics, Inc. (IDI), and NIH. Different reaction stoichiometry (pNIPAAm: antibody molar ratio) was explored to achieve high conjugation efficiency and yield.

Figure 7:
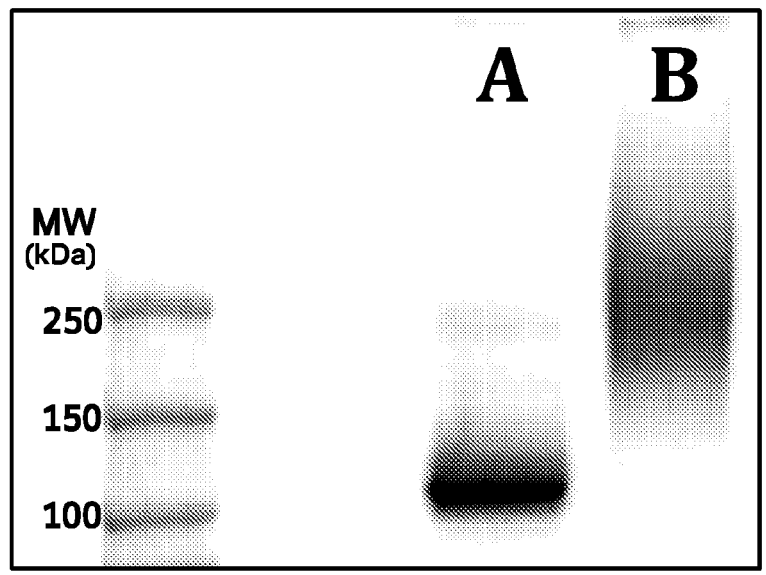
FIG. 7 is an SDS-PAGE gel image used to confirm the conjugation of polymer to antibody as illustrated in FIG. 6.

Sodium dodecyl sulfate polyacrylamide gel electrophoresis (SDS-PAGE) gel (FIG. 7) was used to confirm the polymer-antibody conjugation. Lane A is monoclonal p24 antibody supplied by MBS. Lane B is the pNIPAAm-antibody conjugate. The conjugate shows larger molecular weight than the native p24 antibody and Lane B shows no native p24 antibody band, which confirms complete conjugation.

The binding between the conjugates and p24 (antigen) was evaluated (and confirmed) using ELISA with human plasma samples spiked with p24. The conjugates were constructed by end-conjugating 30,000 molecular weight linear pNIPAAm polymer to monoclonal anti-p24 IgG. The conjugates were initially incubated with the human plasma samples spiked with p24 at room temperature for 10 minutes to establish binding between the conjugate and p24. The solution temperature was then raised to 40° C. for 15 minutes to induce anti-p24 conjugate aggregation. Afterward, the solution was centrifuged at 40° C. for 5 minutes to spin-down the conjugate aggregates with the bound p24. The supernatant was collected and analyzed for the amount of p24 using commercially available p24 ELISA. Antigen (p24)-conjugate binding results in the reduction of p24 in the collected supernatant. When the conjugate:p24 ratio increases from 16:1 to 16000:1, the p24 binding increases from ca. 40 to 90%. The binding reaches ca. 90%, when the conjugate:p24 ratio is ca. 1000:1.

Protein Capture Conjugates—Streptavidin

In certain embodiments, the capture conjugate is a protein conjugate. In an exemplary embodiment, the protein conjugate is a streptavidin conjugate.

Figure 8:
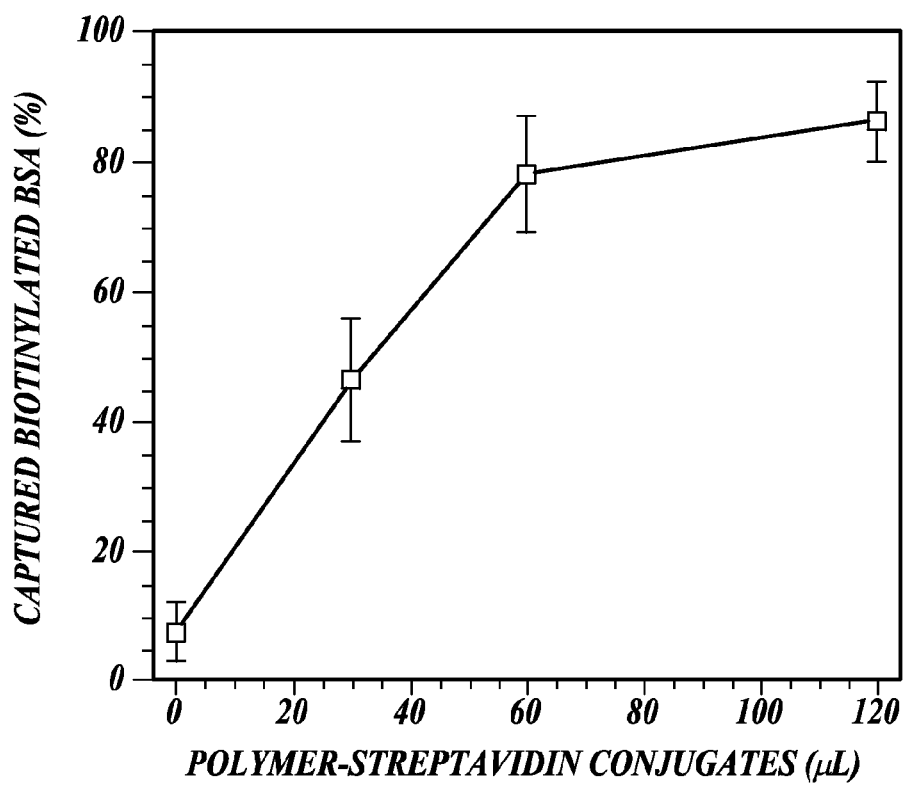
FIG. 8 graphically illustrates the relationship between stimuli-responsive streptavidin conjugates and the percentage of biotinylated diagnostic target captured from a solution in accordance with the embodiments provided herein.

Sample solutions containing 5% serum, 2 mg/mL pNIPAAm mNPs, 0.21 µM fluorescently labeled biotin-BSA were prepared. Different volumes of streptavidin-pNIPAAm conjugate were added to these solutions and allowed 30 minutes incubation at room temp. The streptavidin-pNIPAAm conjugates were synthesized using a route similar to those described above with regard to p24 antibody conjugates. After 5 minutes of heating (ca. 45° C.) to aggregate the pNIPAAm mNPs and streptavidin conjugates, a magnetic field was applied to the heated solution for 2 minutes to achieve magnetic separation. Consequently the fluorescent signals of the collected supernatants were used to determine the amount of unbound biotin-BSA in the solution (i.e., less signal in the supernatant means more aggregates formed and isolated). FIG. 8 graphically illustrates the increase of biotin-BSA separation efficiency when the amount of streptavidin conjugates increases.

Streptavidin Capture Using pH-Responsive Polymers

Figure 9:
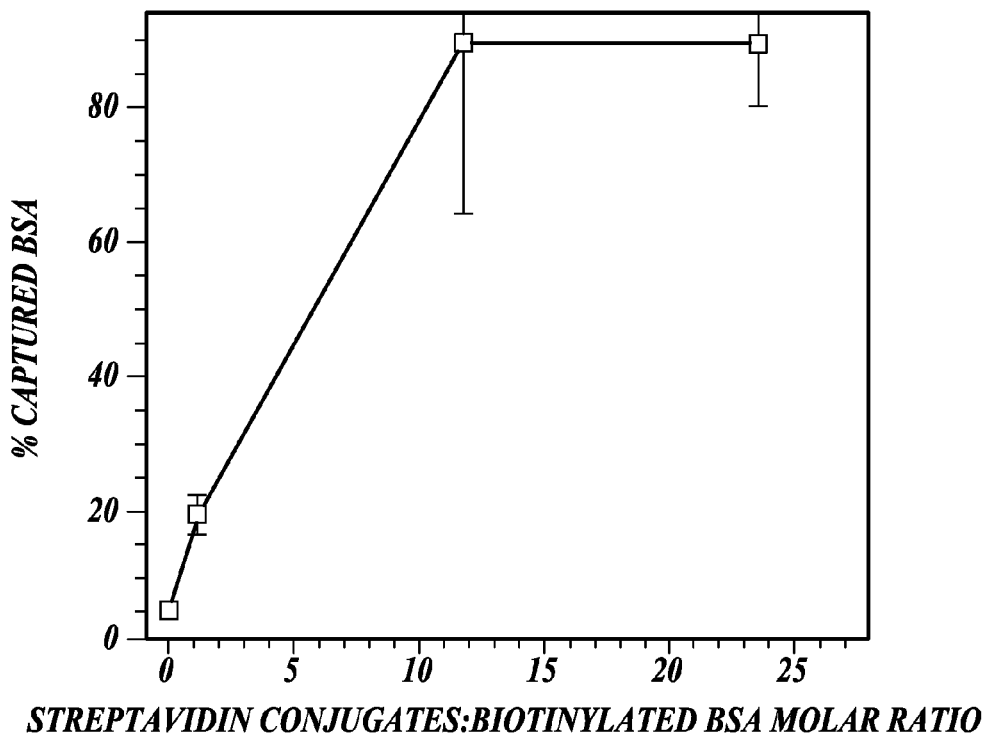
FIG. 9 graphically illustrates the relationship between the percentage of BSA captured versus the molar ratio of streptavidin conjugate to biotinylated BSA in an exemplary embodiment.
Figure 10:
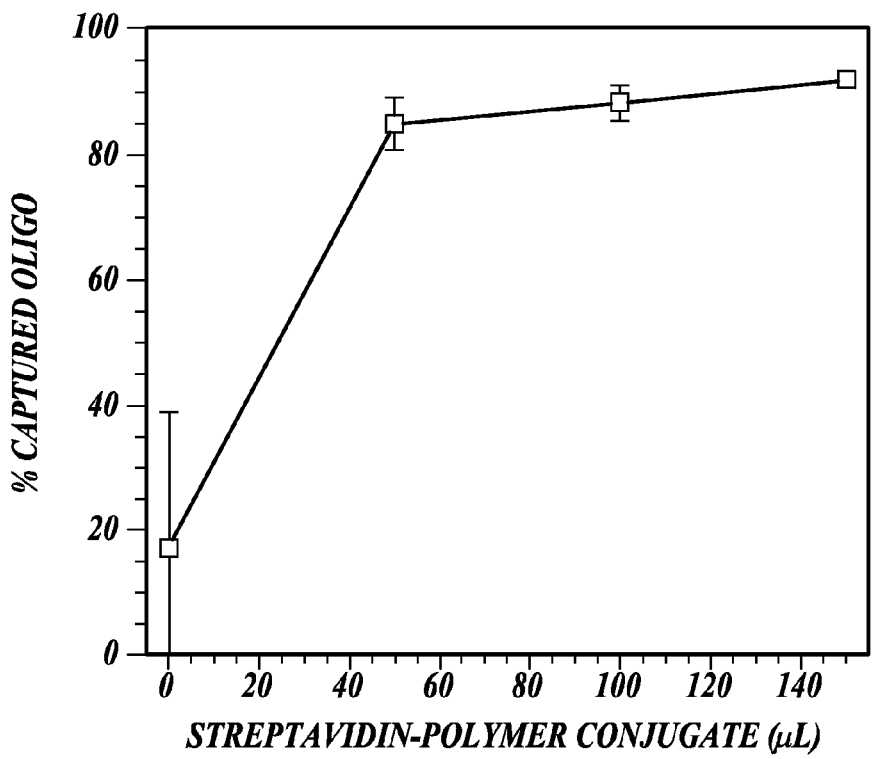
FIG. 10 graphically illustrates the relationship between the percentage of captured oligonucleotide and the volume of streptavidin-polymer conjugate in an exemplary embodiment.

All experiments utilized the samples with constant amount of fluorescently labeled biotinylated BSA solution (ca. 100 µL, pH 7.4, 10% serum). All experiments were carried out at 37° C. by adding various amount of streptavidin, constant amount (6 µL, 10 mg/ml) of biotinylated poly(propylacrylic acid), a pH-responsive polymer, and constant amount pH-responsive magnetic nanoparticles, comprising an iron oxide core with attached poly(N-isopropylacrylamide-co-tert-butyl methacrylate-co-methylacrylic acid, sequentially. After 15 minutes incubation, aggregation of the smart reagent was triggered by adding 50 µL of citrate-phosphate buffer (pH 4.71). Reducing pH protonates the pH-responsive polymers, making them more hydrophobic, and therefore, associative. After five minutes of magnetic separation, the fluorescence signal of the supernatants was used to determine the amount of captured biotinylated BSA. The results are graphically illustrated in FIG. 9 as percent of captured BSA vs. the molar ratio of streptavidin conjugate:biotinylated BSA. The % captured BSA increases along with the molar ratio. When the BSA molecules are not biotinylated, the % captured BSA is similar (ca. 5%) to no streptavidin. The results suggest the biotinylated BSA capture is mediated by streptavidin binding and magnetic separation of smart reagents.

Capture of Oligonucleotides

All experiments utilized samples with constant amount of double helix oligonucleotide ("oligo") containing a biotinylated oligo and a fluorescent labeled complementary oligo. The double helix oligo was annealed to establish hybridization before the magnetic separation. The experiments were carried out by addition various amount of streptavidin-pNIPAAm conjugates and constant amount of temperature-responsive pNIPAAm magnetic nanoparticles. After 15 minutes incubation at room temperature, the magnetic separation was carried out by heating at 45° C. for 5 minutes and applying magnetic field for 2 minutes. The fluorescent signal of the supernatants is used to determine the amount of captured oligo. The results were plot as % Captured oligo vs. the volume of streptavidin-polymer conjugates. The % captured oligo increases along with the conjugate volume. The results suggest the target oligo capture is mediated by biotinylated oligo-streptavidin-polymer conjugates and magnetic separation of smart reagents.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of concentrating a target in a liquid, comprising applying a magnetic field to an aggregate in the liquid to provide a collected aggregate by magnetophoresis, wherein the aggregate comprises:
   (a) a stimuli-responsive magnetic nanoparticle comprising a first stimuli-responsive polymer attached to a magnetic core, wherein the stimuli-responsive magnetic nanoparticle does not include a capture moiety; and
   (b) a stimuli-responsive capture conjugate comprising a second stimuli-responsive polymer attached to a capture moiety, wherein the capture moiety is capable of binding to a target;
   wherein the aggregate is formed through associative interaction between the first stimuli-responsive polymer and the second stimuli-responsive polymer.

2. The method of claim 1, wherein the magnetic field does not induce magnetophoresis in a non-aggregated stimuli-responsive magnetic nanoparticle in the liquid.

3. The method of claim 1 further comprising a step of concentrating the aggregate in the liquid.

4. The method of claim 1, wherein the first stimuli-responsive polymer and the second stimuli-responsive polymer are responsive to stimuli independently selected from the group consisting of temperature, pH, light, photo-irradiation, exposure to an electric field, ionic strength, and combinations thereof.

5. The method of claim 1, wherein the stimuli-responsive capture conjugate further comprises a detector complex comprising a detector moiety and a second capture moiety, wherein the second capture moiety is capable of binding to the target.

6. The method of claim 1, wherein the target is an indicator for a disease or condition.

7. The method of claim 1, wherein the target is selected from the group consisting of an antibody, an antigen, a cell, a nucleic acid, an enzyme, a substrate for an enzyme, a protein, a lipid, a carbohydrate, or other biomarker.

8. The method of claim 1 further comprising a biological sample selected from the group consisting of blood, mucus, urine, tissue, sputum, saliva, feces, a nasal swab, and nasopharyngeal washes.

9. The method of claim 1, wherein the magnetic core is a metal oxide.

10. The method of claim 1 further comprising a second stimuli-responsive capture conjugate comprising a third stimuli-responsive polymer attached to a third capture moiety, wherein the third capture moiety is capable of capturing a second target, wherein the second target is different than the target.

11. A stimuli-responsive reagent, comprising:
  (a) a stimuli-responsive magnetic nanoparticle comprising a first stimuli-responsive polymer attached to a magnetic core, wherein the stimuli-responsive magnetic nanoparticle does not include a capture moiety; and
  (b) a stimuli-responsive capture conjugate comprising a second stimuli-responsive polymer attached to a first capture moiety, wherein the first capture moiety is capable of binding to a target.

12. The stimuli-responsive reagent of claim 11, wherein the first stimuli-responsive polymer and the second stimuli-responsive polymer are responsive to stimuli independently selected from the group consisting of temperature, pH, light, photo-irradiation, exposure to an electric field, ionic strength, and combinations thereof.

13. The stimuli-responsive reagent of claim 11, wherein the stimuli-responsive reagent further comprises a detector complex comprising a detector moiety and a second capture moiety, wherein the second capture moiety is capable of binding to the target.

14. The stimuli-responsive reagent of claim 11, wherein the target is an indicator for a disease or condition.

15. The stimuli-responsive reagent of claim 11, wherein the target is selected from the group consisting of an antibody, an antigen, a cell, a nucleic acid, an enzyme, a substrate for an enzyme, a protein, a lipid, a carbohydrate, or other biomarker.

16. The stimuli-responsive reagent of claim 11, wherein the magnetic core is a metal oxide.

17. The stimuli-responsive reagent of claim 11 further comprising a second stimuli-responsive capture conjugate comprising a third stimuli-responsive polymer attached to a third capture moiety, wherein the third capture moiety is capable of capturing a second target, wherein the second target is different than the target.

18. A method of capturing a target in a liquid, comprising:
  (a) contacting a liquid to be tested for the presence of a target with a stimuli-responsive reagent for a pre-determined period of time sufficient to effect binding of the target, if present, to the stimuli-responsive reagent, wherein the stimuli-responsive reagent comprises:
    (i) a stimuli-responsive magnetic nanoparticle comprising a first stimuli-responsive polymer attached to a magnetic core, wherein the stimuli-responsive magnetic nanoparticle does not include a capture moiety; and
    (ii) a stimuli-responsive capture conjugate comprising a second stimuli-responsive polymer attached to a capture moiety, wherein the capture moiety is capable of binding to a target;
  (b) applying an effective stimulus to provide an aggregate in the liquid formed through associative interaction between the first stimuli-responsive polymer and the second stimuli-responsive polymer, wherein the aggregate comprises the stimuli-responsive magnetic nanoparticle and the stimuli-responsive capture conjugate, and wherein the capture moiety is bound to the target when the target is present in the liquid;
  (c) subjecting the aggregate to a magnetic field to magnetophorese the aggregate to a site within the liquid to provide a magnetophoresed aggregate in the liquid; and
  (d) analyzing the magnetophoresed aggregate to determine if the target is present.

19. The method of claim 18 further comprising binding a detector complex to the target, said detector complex comprising a second capture moiety capable of binding to the target and a reporting moiety.

20. The method of claim 19, wherein the step of analyzing the magnetophoresed aggregate comprises photoluminescence analysis.

21. The method of claim 1, wherein the stimuli-responsive capture conjugate does not include a magnetic nanoparticle.

22. The method of claim 1, wherein the stimuli-responsive magnetic nanoparticle consists of the first stimuli-responsive polymer attached to the magnetic core.

23. The stimuli-responsive reagent of claim 11, wherein the stimuli-responsive capture conjugate does not include a magnetic nanoparticle.

24. The stimuli-responsive reagent of claim 11, wherein the stimuli-responsive magnetic nanoparticle consists of the first stimuli-responsive polymer attached to the magnetic core.

25. The method of claim 18, wherein the stimuli-responsive capture conjugate does not include a magnetic nanoparticle.

26. The method of claim 18, wherein the stimuli-responsive magnetic nanoparticle consists of the first stimuli-responsive polymer attached to the magnetic core.

* * * * *